US011958886B2

(12) United States Patent
Ghivizzani

(10) Patent No.: US 11,958,886 B2
(45) Date of Patent: *Apr. 16, 2024

(54) IL-1RA CDNAS

(71) Applicant: University of Florida Research Foundation, Incorporated, Gainesville, FL (US)

(72) Inventor: Steven C. Ghivizzani, Gainesville, FL (US)

(73) Assignee: University of Florida Research Foundation, Incorporated, Gainesville, FL (US)

(*) Notice: Subject to any disclaimer, the term of this patent is extended or adjusted under 35 U.S.C. 154(b) by 740 days.

This patent is subject to a terminal disclaimer.

(21) Appl. No.: 16/467,141

(22) PCT Filed: Dec. 7, 2017

(86) PCT No.: PCT/US2017/065173
§ 371 (c)(1),
(2) Date: Jun. 6, 2019

(87) PCT Pub. No.: WO2018/106956
PCT Pub. Date: Jun. 14, 2018

(65) Prior Publication Data
US 2020/0071371 A1 Mar. 5, 2020

Related U.S. Application Data

(60) Provisional application No. 62/486,944, filed on Apr. 18, 2017, provisional application No. 62/431,336, filed on Dec. 7, 2016.

(51) Int. Cl.
*C07K 14/47* (2006.01)
*C12N 15/86* (2006.01)
*A61K 9/00* (2006.01)

(52) U.S. Cl.
CPC .......... *C07K 14/4703* (2013.01); *C12N 15/86* (2013.01); *A61K 9/0019* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 5,747,072 A | 5/1998 | Davidson et al. | |
| 5,756,283 A | 5/1998 | Wilson et al. | |
| 6,040,183 A | 3/2000 | Ferrari et al. | |
| 6,083,716 A | 7/2000 | Wilson et al. | |
| 6,093,570 A | 7/2000 | Ferrari et al. | |
| 6,429,001 B1 | 8/2002 | Hardy | |
| 6,482,634 B1 | 11/2002 | Wilson et al. | |
| 6,491,907 B1 | 12/2002 | Rabinowitz et al. | |
| 6,548,286 B1 | 4/2003 | Samulski et al. | |
| 6,943,153 B1 | 9/2005 | Manning et al. | |
| 6,951,758 B2 | 10/2005 | Ferrari et al. | |
| 7,037,492 B2 | 5/2006 | Glorioso et al. | |
| 7,229,823 B2 | 6/2007 | Samulski et al. | |
| 7,439,065 B2 | 10/2008 | Ferrari et al. | |
| 7,452,696 B2 | 11/2008 | Chen et al. | |
| 7,465,583 B2 | 12/2008 | Samulski et al. | |
| 7,790,154 B2 | 9/2010 | Samulski et al. | |
| 7,892,809 B2 | 2/2011 | Bowles et al. | |
| 7,892,824 B2 | 2/2011 | Duan et al. | |
| 8,361,457 B2 | 1/2013 | Samulski et al. | |
| 8,529,885 B2 | 9/2013 | Tak et al. | |
| 8,736,207 B2 | 5/2014 | Ritter et al. | |
| 8,809,058 B2 | 8/2014 | Ferrari et al. | |
| 8,999,948 B2 | 4/2015 | Tubert et al. | |
| 9,216,205 B2 | 12/2015 | Chakraborty et al. | |
| 11,207,382 B2 | 12/2021 | Ghivizzani | |
| 2004/0237145 A1 | 11/2004 | Graham et al. | |
| 2005/0271618 A1 | 12/2005 | Raibekas et al. | |
| 2006/0014966 A1 | 1/2006 | Lee et al. | |
| 2007/0009899 A1 | 1/2007 | Mounts | |
| 2007/0042462 A1 | 2/2007 | Hildinger | |
| 2007/0128177 A1 | 6/2007 | Burstein et al. | |
| 2008/0166762 A1 | 7/2008 | Shivraj et al. | |
| 2008/0187576 A1 | 8/2008 | Ghivizzani et al. | |
| 2009/0104155 A1 | 4/2009 | Goodrich et al. | |
| 2009/0105148 A1 | 4/2009 | Aikawa et al. | |
| 2011/0076285 A1 | 3/2011 | Stalmans et al. | |
| 2012/0232130 A1 | 9/2012 | Cepko et al. | |
| 2012/0237587 A1 | 9/2012 | Wehling et al. | |

(Continued)

FOREIGN PATENT DOCUMENTS

| | | |
|---|---|---|
| CN | 103509100 A | 1/2014 |
| CN | 104245941 A | 12/2014 |

(Continued)

OTHER PUBLICATIONS

Goodrich et al, Optimization of scAAVIL-1ra in Vitro and in Vivo to Deliver High Levels of Therapeutic Protein for Treatment of Osteoarthritis. Molecular Therapy-Nucleic Acids (2013) 2, e70.*
Watson et al, Exploring the capacity of local self-complimentary aav mediated delivery of equine IL-1Ra to block the symptoms and progression of osteoarthritis in an equine model. Molecular Therapy, (Jun. 2014) vol. 22, Supp. SUPPL. 1, pp. S292. Abstract No. 757.*
Frisbie et al, Treatment of experimental equine osteoarthritis by in vivo delivery of the equine interleukin-1 receptor antagonist gene. Gene Therapy (2002) 9, 12-20.*
Watson et al, ScAAV provides sustained expression of a homologous therapeutic transgene in large mammalian joints, with enhanced expression in osteoarthritis. Molecular Therapy, (Jun. 2013) vol. 21, Supp. SUPPL. 1, pp. S36. Abstract No. 88.*

(Continued)

*Primary Examiner* — Hope A Robinson
(74) *Attorney, Agent, or Firm* — Wolf, Greenfield & Sacks, P.C.

(57) ABSTRACT

The present disclosure relates to compositions and methods for treatment of degenerative conditions of large weight-bearing joints, such as osteoarthritis, by intra-articular delivery of a codon-modified IL-1Ra encoding gene.

18 Claims, 13 Drawing Sheets

Specification includes a Sequence Listing.

(56) References Cited

U.S. PATENT DOCUMENTS

| | | |
|---|---|---|
| 2013/0217864 A1 | 8/2013 | Cho et al. |
| 2013/1021786 | 8/2013 | Cho et al. |
| 2013/0295614 A1 | 11/2013 | Hareedran et al. |
| 2014/0107189 A1 | 4/2014 | Bancel et al. |
| 2014/0141067 A1 | 5/2014 | Bancel et al. |
| 2014/0234255 A1 | 8/2014 | Lai et al. |
| 2015/0031083 A1 | 1/2015 | Lee et al. |
| 2015/0050238 A1 | 2/2015 | Kamath |
| 2015/0218586 A1 | 8/2015 | Schleef |
| 2015/0353938 A1 | 12/2015 | Ye et al. |
| 2015/0361452 A1 | 12/2015 | Ruan et al. |
| 2016/0068844 A1 | 3/2016 | Wadsworth et al. |
| 2019/0381140 A1 | 12/2019 | Bartlett |
| 2022/0175887 A1 | 6/2022 | Bartlett et al. |

FOREIGN PATENT DOCUMENTS

| | | |
|---|---|---|
| CN | 109843306 A | 6/2019 |
| JP | 2002-538770 A | 11/2002 |
| JP | 2003-518371 A | 6/2003 |
| JP | 2010-516252 A | 5/2010 |
| JP | 2015-518816 A | 7/2015 |
| KR | 20030086429 A | 11/2003 |
| KR | 20030089291 A | 11/2003 |
| KR | 20120041139 A | 4/2012 |
| WO | WO 1995/016353 A1 | 6/1995 |
| WO | WO 2001/042304 A1 | 6/2001 |
| WO | WO 2002/038782 A2 | 5/2002 |
| WO | WO 2002/062375 A1 | 8/2002 |
| WO | WO 2004/092211 A1 | 10/2004 |
| WO | WO 2007/039699 A3 | 5/2007 |
| WO | WO 2008/088895 A2 | 7/2008 |
| WO | WO 2008/132485 A2 | 11/2008 |
| WO | WO 2012/047093 A1 | 4/2012 |
| WO | WO 2013/151672 A2 | 10/2013 |
| WO | WO 2014/170470 A1 | 10/2014 |
| WO | WO 2015/018860 A1 | 2/2015 |
| WO | WO 2015/031392 A1 | 3/2015 |
| WO | WO 2015/044292 A1 | 4/2015 |
| WO | WO 2015/158749 A3 | 10/2015 |
| WO | WO 2015/168666 A2 | 11/2015 |
| WO | WO 2018/035441 A1 | 2/2018 |
| WO | WO 2018/035451 A1 | 2/2018 |
| WO | WO 2018/035457 A1 | 2/2018 |
| WO | WO 2018/106956 A2 | 6/2018 |

OTHER PUBLICATIONS

Goodrich et al, Optimization of scAAVIL-1ra in Vitro and in Vivo to Deliver High Levels of Therapeutic Protein for Treatment of Osteoarthritis. Molecular Therapy-Nucleic Acids (2013) 2, e70. 10 pages.*
U.S. Appl. No. 17/555,320, filed Dec. 17, 2021, Bartlett et al.
EP 17878272.8, Jun. 9, 2020, Extended European Search Report.
EP 17842207.7, Mar. 3, 2020, Extended European Search Report.
Extended European Search Report for Application No. EP 17878272.8 dated Jun. 9, 2020.
Extended European Search Report for Application No. EP 17842207.7 dated Mar. 3, 2020.
Bowles et al., Phase 1 gene therapy for Duchenne muscular dystrophy using a translational optimized AAV vector. Mol Ther. Feb. 2012;20(2):443-55. doi: 10.1038/mt.2011.237. Epub Nov. 8, 2011.
Chang et al., The production and characterization of a modified recombinant interleukin-1 receptor antagonist. Immunol Invest. Jul. 1996;25(4):355-68.
Fath et al., Multiparameter RNA and codon optimization: a standardized tool to assess and enhance autologous mammalian gene expression. PLoS One. Mar. 3, 2011;6(3):e17596. doi: 10.1371/journal.pone.0017596. Erratum in: PLoS One. 2011;6(3). doi: 10.1371/annotation/039deb02-bbe7-406c-a876-341cc4f3fefa.
Garmory et al., DNA vaccines: improving expression of antigens. Genet Vaccines Ther. Sep. 16, 2003;1(1):2. doi: 10.1186/1479-0556-1-2.
Goodrich et al., scAAVIL-1ra dosing trial in a large animal model and validation of long-term expression with repeat administration for osteoarthritis therapy. Gene Ther. Jul. 2015;22(7):536-45. doi: 10.1038/gt.2015.21. Epub Apr. 23, 2015.
He et al., Lentivirus transduced interleukin-1 receptor antagonist gene expression in murine bone marrow-derived mesenchymal stem cells in vitro. Mol Med Rep. Sep. 2015;12(3):4063-4070. doi: 10.3892/mmr.2015.4003. Epub Jun. 26, 2015.
Husain et al., Long-term AAV vector gene and protein expression in mouse brain from a small pan-cellular promoter is similar to neural cell promoters. Gene Ther. Jul. 2009;16(7):927-32. doi: 10.1038/gt.2009.52. Epub May 21, 2009.
Kay et al., Intra-articular gene delivery and expression of interleukin-1Ra mediated by self-complementary adeno-associated virus. J Gene Med. Jul. 2009;11(7):605-14.
Kay et al., Self-Complementary Vectors Significantly Enhance AAV-Mediated Gene Transfer to Joint Tissues. Mol Ther. Jan. 1, 2006;13:S420-1.
Makarov et al., Suppression of experimental arthritis by gene transfer of interleukin 1 receptor antagonist cDNA. Proc Natl Acad Sci U S A. Jan. 9, 1996;93(1):402-6. doi: 10.1073/pnas.93.1.402.
Pan et al., Therapy and prevention of arthritis by recombinant adeno-associated virus vector with delivery of interleukin-1 receptor antagonist. Arthritis Rheum. Feb. 2000;43(2):289-97.
[No Author Listed] UniProt Accession No. O18999. Sep. 21, 2022. 7 pages.
Alexaki et al., Effects of codon optimization on coagulation factor IX translation and structure: Implications for protein and gene therapies. Sci Rep. Oct. 29, 2019;9(1):15449. doi: 10.1038/s41598-019-51984-2.
Chupradit et al., Validation of Promoters and Codon Optimization on CRISPR/Cas9-Engineered Jurkat Cells Stably Expressing αRep4E3 for Interfering with HIV-1 Replication. Int J Mol Sci. Nov. 30, 2022;23(23):15049. doi: 10.3390/ijms232315049.
Del Rey et al., Transcriptome analysis reveals specific changes in osteoarthritis synovial fibroblasts. Ann Rheum Dis. Feb. 2012;71(2):275-80. doi: 10.1136/annrheumdis-2011-200281. Epub Oct. 21, 2011.
Klein et al., Functional testing of thousands of osteoarthritis-associated variants for regulatory activity. Nat Commun. Jun. 4, 2019;10(1):2434. doi: 10.1038/s41467-019-10439-y.
McCoy, Animal Models of Osteoarthritis: Comparisons and Key Considerations. Vet Pathol. Sep. 2015;52(5):803-18. doi: 10.1177/0300985815588611. Epub Jun. 10, 2015.
McIlwraith et al., The horse as a model of naturally occurring osteoarthritis. Bone Joint Res. Nov. 1, 2012;1(11):297-309. doi: 10.1302/2046-3758.111.2000132.
U.S. Appl. No. 16/326,488, filed Feb. 19, 2019, Bartlett.
PCT/US2017/065173, May 9, 2018, International Search Report and Written Opinion.
PCT/US2017/065173, Jun. 11, 2019, International Preliminary Report on Patentability.
PCT/US2017/047589, Nov. 8, 2017, International Search Report and Written Opinion.
PCT/US2017/047589, Feb. 19, 2019, International Preliminary Report on Patentability.
International Search Report and Written Opinion for Application No. PCT/US2017/065173 dated May 6, 2018.
International Preliminary Report on Patentability for Application No. PCT/US2017/065173 dated Jun. 11, 2019.
International Search Report and Written Opinion for Application No. PCT/US2017/047589 dated Nov. 8, 2017.
International Preliminary Report on Patentability for Application No. PCT/US2017/047589 dated Feb. 19, 2019.
Altschul et al., Basic local alignment search tool. J Mol Biol. Oct. 5, 1990; 215(3):403-10.
Cao et al. Therapeutic targeting and rapid mobilization of endosteal HSC using a small molecule integrin antagonist. Nature Communications. 2016; 7:11007.
Corpet, Multiple sequence alignment with hierarchical clustering. Nucleic Acids Res. Nov. 25, 1988; 16(22):10881-90.

(56) References Cited

OTHER PUBLICATIONS

Evans et al., Clinical trial to assess the safety, feasibility, and efficacy of transferring a potentially anti-arthritic cytokine gene to human joints with rheumatoid arthritis. Hum Gene Ther. Jun. 20, 1996; 7(10):1261-80.
Evans et al., Gene transfer to human joints: progress toward a gene therapy of arthritis. Proc Natl Acad Sci U S A. Jun. 14, 2005; 102(24):8698-703. Epub Jun. 6, 2005.
Frisbie et al., Treatment of experimental equine osteoarthritis by in vivo delivery of the equine interleukin-1 receptor antagonist gene. Gene Ther. Jan. 2002; 9(1):12-20.
Genbank: AY026462.1, Canis familiaris interleukin-1 receptor antagonist mRNA, complete cds. 68.71.72.74 GenBank. Feb. 12, 2001. pp. 1-12. Retrieved from the Internet: https://www.ncbi.nlm.nih.gov/nuccore/AY026462.1 on Oct. 14, 2017.
Goodrich et al. Optimization of scAAVIL-1ra in Vitro and in Vivo to Deliver High Levels of Therapeutic Protein for Treatment of Osteoarthritis. Mol Ther Nucleic Acids. Feb. 5, 2013;2:e70. doi: 10.1038/mtna.2012.61.
Goss et al., Safety, Tolerability and Pharmacokinetics of Abt-981, an IL-1A and IL-1β Dual Target Biologic Drug in Development for Osteoarthritis, following Single Dose Administration in Healthy Subjects. Annals of the Rheumatic Diseases 2014; 73:755-756.
Higgins et al., CLUSTAL: a package for performing multiple sequence alignment on a microcomputer. Gene. Dec. 15, 1988; 73(1):237-44.
Higgins et al., Fast and sensitive multiple sequence alignments on a microcomputer. Comput Appl Biosci. Apr. 1989; 5(2):151-3.
Huang et al., Parallelization of a local similarity algorithm. Parallelization of a local similarity algorithm. Comput Appl Biosci. Apr. 1992; 8(2):155-65.
Kamath et al., Simultaneous Targeting of IL-1α and IL-1β by a Dual-Variable-Domain Immunoglobulin (DVD-IgTM) Prevents Cartilage Degradation in Preclinical Models of Osteoarthritis. Osteoarthritis and Cartilage. 2011; 19S1:S64.
Kent, BLAT—the BLAST-like alignment tool. Genome Res. Apr. 2002; 12(4):656-64.
Lacy et al., Generation and characterization of ABT-981, a dual variable domain immunoglobulin (DVD-Ig(TM)) molecule that specifically and potently neutralizes both IL-1α and IL-1β. MAbs. 2015; 7(3):605-19. doi: 10.1080/19420862.2015.1026501.

Needleman et al., A general method applicable to the search for similarities in the amino acid sequence of two proteins. J Mol Biol. Mar. 1970; 48(3):443-53.
Pearson et al., Improved tools for biological sequence comparison. Proc Natl Acad Sci U S A. Apr. 1988; 85(8):2444-8.
Pepinsky et al., Comparative assessment of the ligand and metal ion binding properties of integrins alpha9beta1 and alpha4beta1. Biochemistry. Jun. 4, 2002; 41(22):7125-41.
Smith et al., Comparison of biosequences. Adv. Appl. Math. Dec. 1981. 2:482-489.
Van De Loo et al., An inflammation-inducible adenoviral expression system for local treatment of the arthritic joint. Gene Ther. Apr. 2004; 11(7):581-90.
Wang et al., Dual Variable Domain-Immunoglobulin (Dvd-Igâ„¢) Abt-981 Simultaneously and Dose-Dependently Inhibits Interleukin-1 Î'lpha and -1 Î3 eta in Subjects with Knee Osteoarthritis. 2015 ACR/ARHP Annual Meeting Abstract No. 318.
Wang et al., Interleukin-1 Dual Variable Domain Immunoglobulin, a new Potential Treatment for Osteoarthritis. Osteoarthritis and Cartilage. 2014; 22:S462-S463.
Wang et al., Interleukin-1 Dual Variable-Domain Immunoglobulin Reduces Multiple Imflammatory Markers in Knee Osteoarthritis patients. Scientific Abstracts. 2014; SAT0448.
Wang et al., Interleukin-1 Dual-Variable Domain Immunoglobulin Reduces Multiple Inflammatory Markers in Knee Osteoarthritis Patients. 2014 ACR/ARHP Annual Meeting Abstract No. 2237.
Wang et al., Phase 1 Studies of Anti-Interleukin-1 Dual-Variable Domain Immunoglobulin in Healthy Subjects and Patients with Osteoarthritis. Osteoarthritis and Cartilage. 2015; 23:A398-399.
Wang et al., Safety and biodistribution assessment of sc-rAAV2.5IL-1Ra administered via intra-articular injection in a mono-iodoacetate-induced osteoarthritis rat model. Mol Ther Methods Clin Dev. Jan. 13, 2016; 3:15052. doi: 10.1038/mtm.2015.52. eCollection 2016.
Watson et al., scAAV-mediated gene transfer of interleukin-1-receptor antagonist to synovium and articular cartilage in large mammalian joints. Gene Ther. Jun. 2013; 20(6):670-7. doi: 10.1038/gt.2012.81. Epub Nov. 15, 2012.
Wu et al., Molecular construction and optimization of anti-human IL-1alpha/beta dual variable domain immunoglobulin (DVD-Ig) molecules. MAbs. Jul.-Aug. 2009; 1(4):339-47. Epub Jul. 10, 2009.

* cited by examiner

Fig. 1

NATIVE EQUINE IL-1RA cDNA
CODON MODIFIED EQUINE IL-1RA SEQUENCE; <u>KOZAK SEQUENCE</u>

```
              1                                                              60
              ATGGAAATCCGCAGGCGTTC   TGTCAGACACCTAATCTCTC   TCCTCCTTTTCTTGTTCTAC
              : :: :: :::            :   :  :   :: :::       :   :  :   :
GCCACC  ATGGAAATCAGGCGCAGAAG   CGTGCGCCACCTGATCAGCC   TGCTGCTGTTCCTGTTCTAC
              61                                                             120
              TCAGAGACAGCCTGCCACCC   TTTGGGGAAGAGACCCTGCA   AGATGCAAGCCTTCAGAATC
              :::            :        :::    :          :         :    :      :
              AGCGAGACAGCCTGCCACCC   CCTGGGCAAGAGGCCCTGCA   AGATGCAGGCCTTCAGGATC
              121                                                            180
              TGGGATGTTAACCAGAAGAC   CTTCTACATGAGGAATAACC   AACTAGTTGCTGGATACTTG
              :  :  :  :       :          :      : :  :  :       :  :  :   :    :
              TGGGACGTGAACCAGAAAAC   CTTCTACATGCGCAACAACC   AGCTGGTGGCCGGATACCTG
              181                                                            240
              CAAGAATCAAATACTAAATT   ACAAGAAGATAGATGTGG     TGCCCATTGAGCCTGATGCT
               :    :   :   :    ::      :  :    :   :  :          :   :   :  ::
              CAGGAAAGCAACACCAAGCT   GCAGGAAAGATCGACGTCG    TCCCCATCGAGCCCGACGCC
              241                                                            300
              CTATTCCTGGGACTCCATGG   GAGGAAGCTGTGCCTGGCCT   GTGTCAAGTCTGGTGATGAG
              : :  :  :  :  :  :         : :                :  :   :  :  :   :
              CTGTTCCTGGGCCTGCACGG   CAGAAAGCTGTGCCTGGCCT   GCGTGAAGTCCGGCGACGAG
              301                                                            360
              ATTAGGTTCCAATTGGAGGC   AGTTAACATCACTGACCTGA   GCAAGAACAAGGAGGAGAAC
                : :   :: :   :   :       :                               :    :
              ATCAGGTTTCAGCTGGAAGC   CGTGAACATCACCGACCTGA   GCAAGAACAAAGAGGAAAAC
              361                                                            420
              AAGCGCTTCACCTTCATCCG   CTCAAACAGTGGCCCCACCA   CCAGCTTCGAGTCTGCCGCC
                                :       : :  :  :    :                  :: :
              AAGCGCTTCACCTTCATCAG   AAGCAACAGCGGCCCCACCA   CCAGCTTCGAGAGCGCCGCT
              421                                                            480
              TGCCCTGGCTGGTTCCTCTG   CACGGCGCAGGAGGCAGACC   GGCCCGTCAGCCTCACCAAC
                  ::                     :  :    ::  :   :                :
              TGCCCCGGCTGGTTCCTGTG   TACAGCCCAGGAAGCCGACA   GGCCCGTCAGCCTGACCAAC
              481                                                     534
              AAGCCCAAAGAGTCCTTCAT   GGTCACCAAGTTCTACCTCC   AGGAGGACCAGTAG
                           :::                            : :    :    :   :
              AAGCCCAAAGAAAGCTTCAT   GGTCACCAAGTTCTATCTGC   AAGAAGATCAGTAA
```

108/534 (20.2%) mismatch

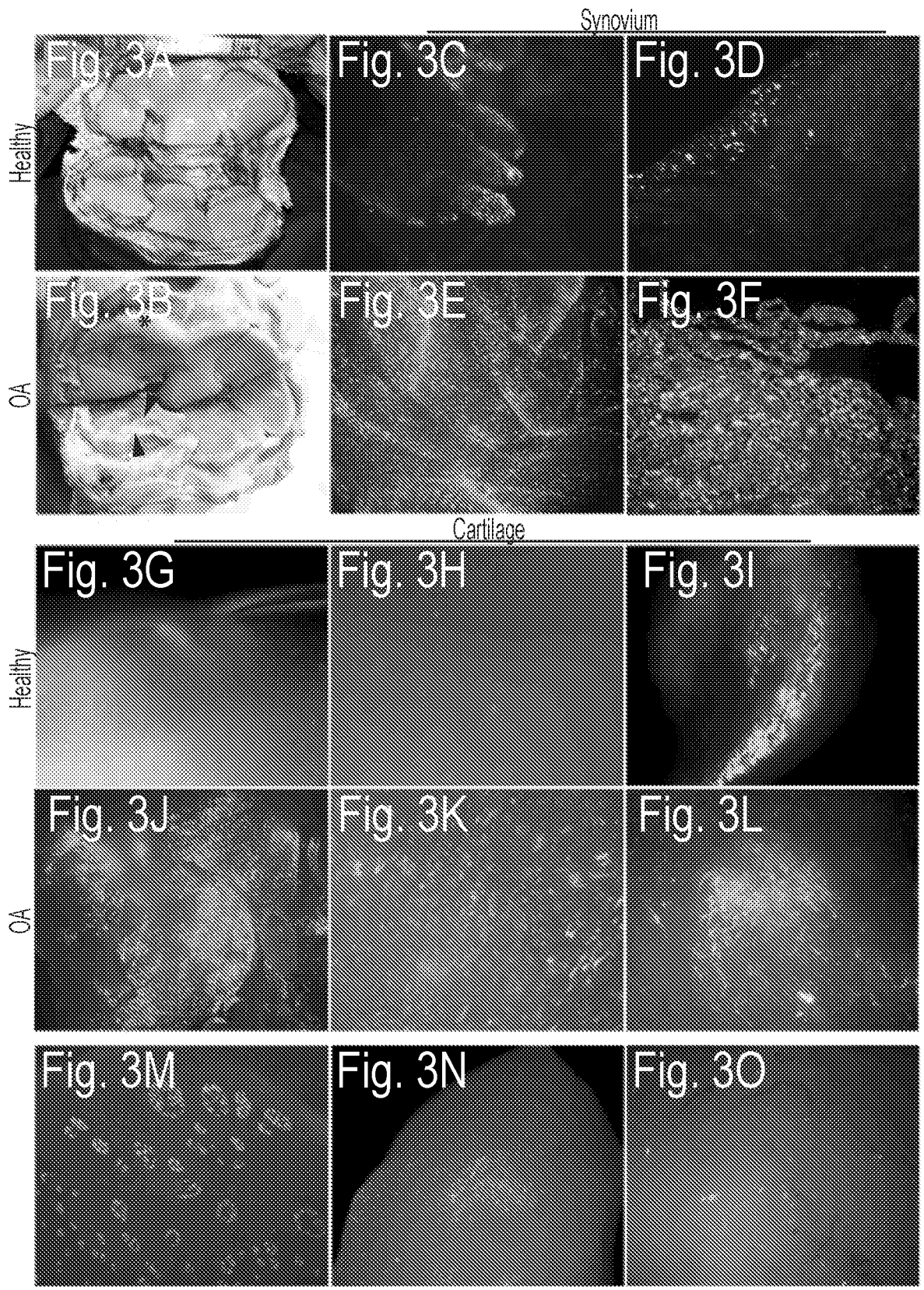

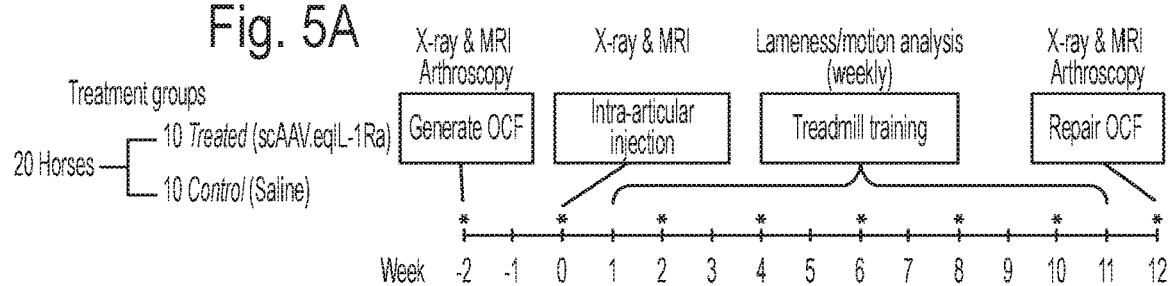
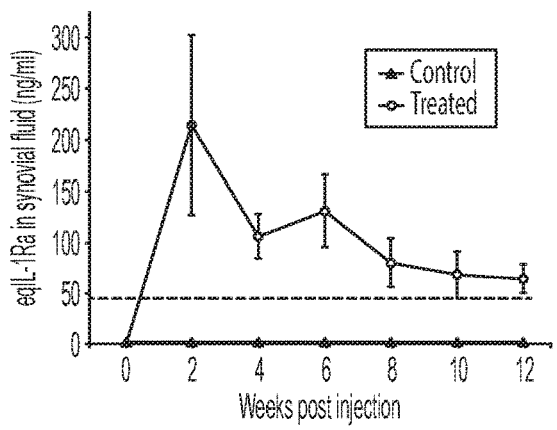
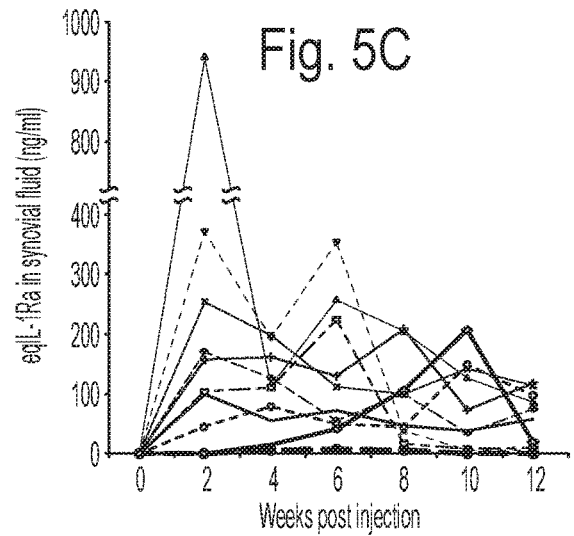
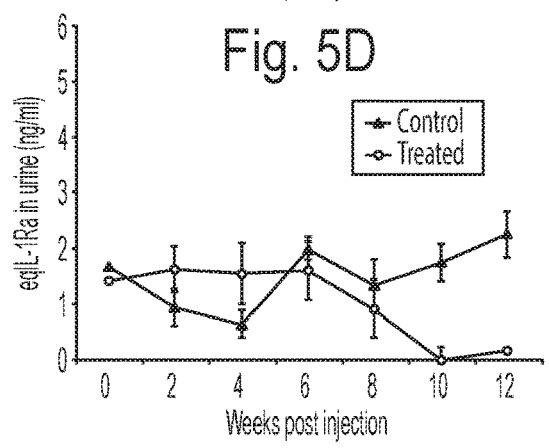
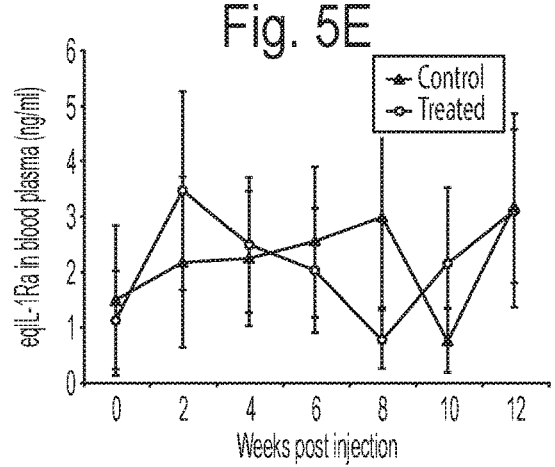
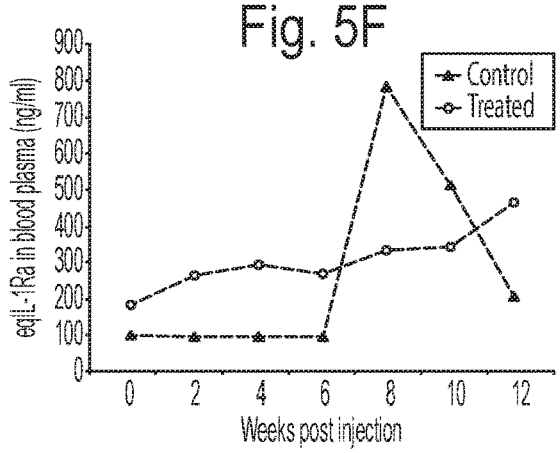
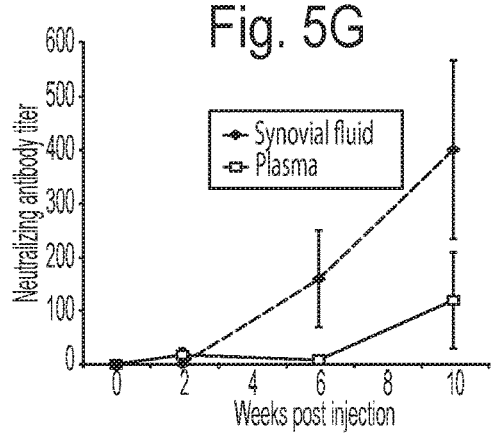

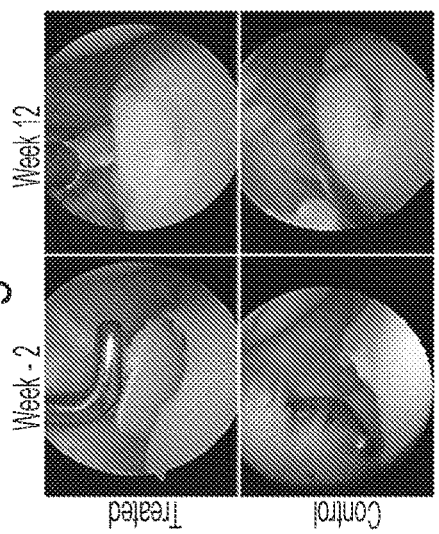
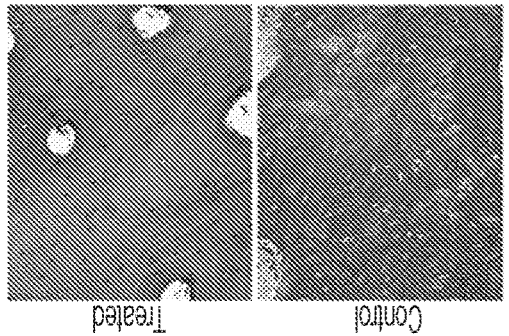
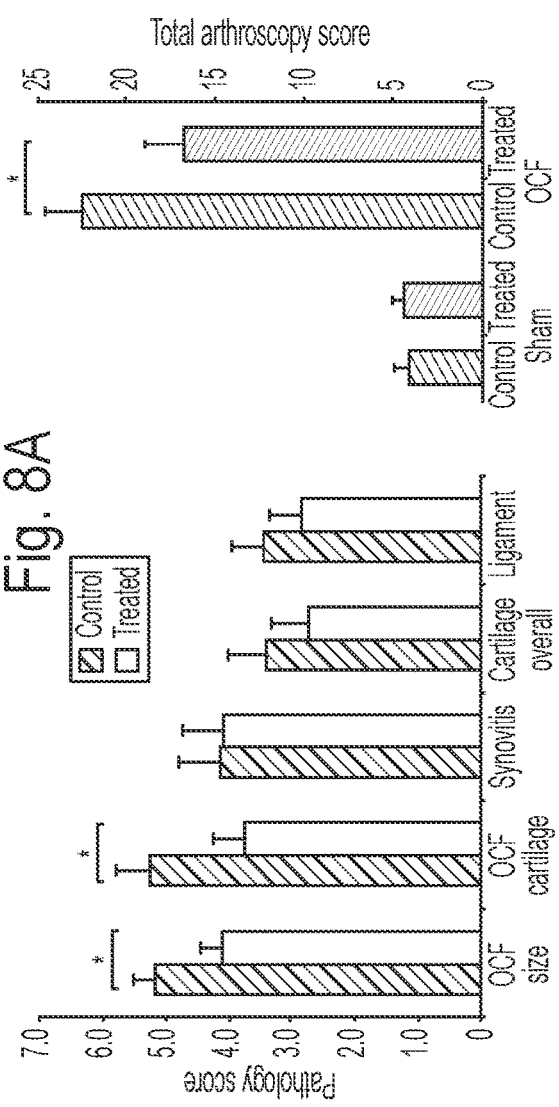
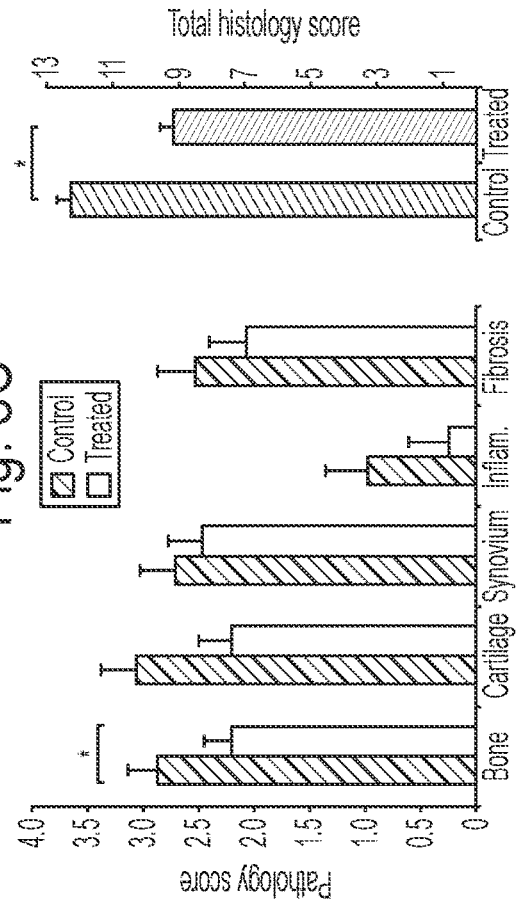

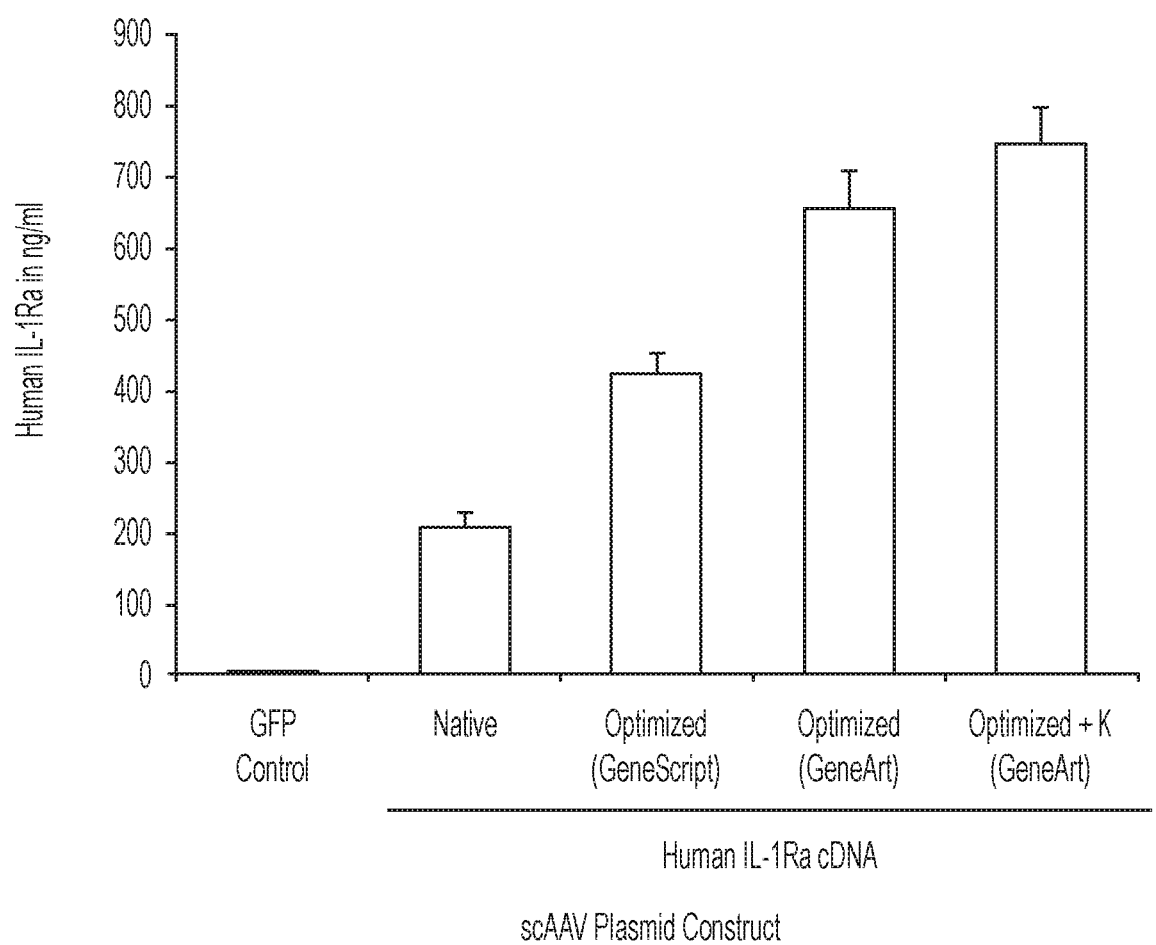

Fig. 13

NATIVE HUMAN IL-1RA cDNA
CODON MODIFIED HUMAN IL-1RA SEQUENCE; <u>KOZAK SEQUENCE</u>

```
                                                                        60
         ATGGAAATCTGCAGAGGCCT CCGCAGTCACCTAATCACTC TCCTCCTCTTCCTGTTCCAT
GCCACCATGGAAATCTGCAGAGGCCT GCGGAGCCACCTGATTACCC TGCTGCTGTTCCTGTTCCAC
                                                                       120
         TCAGAGACGATCTGCCGACC CTCTGGGAGAAAATCCAGCA AGATGCAAGCCTTCAGAATC
         AGCGAGACAATCTGCCGGCC CAGCGGCCGGAAGTCCAGCA AGATGCAGGCCTTCCGGATC
                                                                       180
         TGGGATGTTAACCAGAAGAC CTTCTATCTGAGGAACAACC AACTAGTTGCTGGATACTTG
         TGGGACGTGAACCAGAAAAC CTTCTACCTGCGGAACAACC AGCTGGTGGCCGGATACCTG
                                                                       240
         CAAGGACCAAATGTCAATTT AGAAGAAAAGATAGATGTGG TACCCATTGAGCCTCATGCT
         CAGGGCCCCAACGTGAACCT GGAAGAGAAGATCGACGTGG TGCCCATCGAGCCCCACGCC
                                                                       300
         CTGTTCTTGGGAATCCATGG AGGGAAGATGTGCCTGTCCT GTGTCAAGTCTGGTGATGAG
         CTGTTTCTGGGCATCCACGG CGGCAAGATGTGCCTGAGCT GCGTGAAGTCCGGCGACGAG
                                                                       360
         ACCAGACTCCAGCTGGAGGC AGTTAACATCACTGACCTGA GCGAGAACAGAAAGCAGGAC
         ACAAGACTGCAGCTGGAAGC CGTGAACATCACCGACCTGA GCGAGAACCGGAAGCAGGAC
                                                                       420
         AAGCGCTTCGCCTTCATCCG CTCAGACAGTGGCCCCACCA CCAGTTTTGAGTCTGCCGCC
         AAGAGATTCGCCTTCATCAG AAGCGACAGCGGCCCCACCA CCAGCTTTGAGAGCGCCGCC
                                                                       480
         TGCCCCGGTTGGTTCCTCTG CACAGCGATGGAAGCTGACC AGCCCGTCAGCCTCACCAAT
         TGCCCCGGCTGGTTCCTGTG TACAGCCATGGAAGCCGACC AGCCCGTGTCCCTGACAAAC
                                                                       534
         ATGCCTGACGAAGGCGTCAT GGTCACCAAATTCTACTTCC AGGAGGACGAGTAG
         ATGCCCGACGAGGGCGTGAT GGTCACCAAGTTCTATTTTC AAGAAGATGAGTAA
```

105/534 changes from native sequence (19.6%)

SEQUENCE LISTING

```
<160> NUMBER OF SEQ ID NOS: 11

<210> SEQ ID NO 1
<211> LENGTH: 534
<212> TYPE: DNA
<213> ORGANISM: Equus caballus

<400> SEQUENCE: 1
atggaaatcc gcaggcgttc tgtcagacac ctaatctctc tcctcctttt cttgttctac     60
tcagagacag cctgccaccc tttggggaag agaccctgca agatgcaagc cttcagaatc    120
tgggatgtta accagaagac cttctacatg aggaataacc aactagttgc tggatacttg    180
caagaatcaa atactaaatt acaagagaag atagatgtgg tgcccattga gcctgatgct    240
ctattcctgg gactccatgg gaggaagctg tgcctggcct gtgtcaagtc tggtgatgag    300
attaggttcc aattggaggc agttaacatc actgacctga gcaagaacaa ggaggagaac    360
aagcgcttca ccttcatccg ctcaaacagt ggccccacca ccagcttcga gtctgccgcc    420
tgccctggct ggttcctctg cacggcgcag gaggcagacc ggcccgtcag cctcaccaac    480
aagcccaaag agtccttcat ggtcaccaag ttctacctcc aggaggacca gtag          534

<210> SEQ ID NO 2
```

```
<211> LENGTH: 534
<212> TYPE: DNA
<213> ORGANISM: Artificial Sequence
<220> FEATURE:
<223> OTHER INFORMATION: Synthetic Polynucleotide

<400> SEQUENCE: 2
atggaaatca ggcgcagaag cgtgcgccac ctgatcagcc tgctgctgtt cctgttctac      60
agcgagacag cctgccaccc cctgggcaag aggccctgca agatgcaggc cttcaggatc     120
tgggacgtga accagaaaac cttctacatg cgcaacaacc agctggtggc cggatacctg     180
caggaaagca caccaagct gcaggaaaag atcgacgtcg tccccatcga gcccgacgcc     240
ctgttcctgg gcctgcacgg cagaaagctg tgcctggcct gcgtgaagtc cggcgacgag     300
atcaggtttc agctggaagc cgtgaacatc accgacctga gcaagaacaa agaggaaaac     360
aagcgcttca ccttcatcag aagcaacagc ggccccacca ccagcttcga gagcgccgct     420
tgccccggct ggttcctgtg tacagcccag gaagccgaca ggcccgtcag cctgaccaac     480
aagcccaaag aaagcttcat ggtcaccaag ttctatctgc aagaagatca gtaa           534

<210> SEQ ID NO 3
<211> LENGTH: 540
<212> TYPE: DNA
<213> ORGANISM: Artificial Sequence
<220> FEATURE:
<223> OTHER INFORMATION: Synthetic Polynucleotide

<400> SEQUENCE: 3
gccaccatgg aaatcaggcg cagaagcgtg cgccacctga tcagcctgct gctgttcctg      60
ttctacagcg agacagcctg ccaccccctg ggcaagaggc cctgcaagat gcaggccttc     120
aggatctggg acgtgaacca gaaaaccttc tacatgcgca acaaccagct ggtggccgga     180
tacctgcagg aaagcaacac caagctgcag gaaaagatcg acgtcgtccc catcgagccc     240
gacgccctgt tcctgggcct gcacggcaga aagctgtgcc tggcctgcgt gaagtccggc     300
gacgagatca ggtttcagct ggaagccgtg aacatcaccg acctgagcaa gaacaaagag     360
gaaaacaagc gcttcacctt catcagaagc aacagcggcc ccaccaccag cttcgagagc     420
gccgcttgcc ccggctggtt cctgtgtaca gcccaggaag ccgacaggcc cgtcagcctg     480
accaacaagc ccaaagaaag cttcatggtc accaagttct atctgcaaga agatcagtaa     540

<210> SEQ ID NO 4
<211> LENGTH: 750
<212> TYPE: DNA
<213> ORGANISM: Artificial Sequence
<220> FEATURE:
<223> OTHER INFORMATION: Synthetic Polynucleotide

<400> SEQUENCE: 4
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat     300
agtaacgcca atagggactt tccattgacg tcaatgggtg gagtatttac ggtaaactgc     360
ccacttggca gtacatcaag tgtatcatat gccaagtccg cccccattg acgtcaatga     420 cggtaaatgg cccgcctggc attatgccca gtacatgacc ttacgggact tcctacttg     480
```

```
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc                                     750
```

```
<210> SEQ ID NO 5
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 5
cacgctgttt gacctccata gaagacac                                        28

<210> SEQ ID NO 6
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 6
ttctttgatt tgcaccacca ccggatccg                                       29

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
ccagcacgat gaagatcaag                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 8
gtggacaatg aggccagaat                                                 20

<210> SEQ ID NO 9
<211> LENGTH: 534
<212> TYPE: DNA
<213> ORGANISM: Homo sapiens

<400> SEQUENCE: 9
atggaaatct gcagaggcct ccgcagtcac ctaatcactc tcctcctctt cctgttccat    60
tcagagacga tctgccgacc ctctgggaga aaatccagca agatgcaagc cttcagaatc    120
tgggatgtta accagaagac cttctatctg aggaacaacc aactagttgc tggatacttg    180
caaggaccaa atgtcaattt agaagaaaag atagatgtgg tacccattga gcctcatgct    240
ctgttcttgg gaatccatgg agggaagatg tgcctgtcct gtgtcaagtc tggtgatgag    300
accagactcc agctggaggc agttaacatc actgacctga gcgagaacag aaagcaggac    360
```

```
aagcgcttcg ccttcatccg ctcagacagt ggccccacca ccagttttga gtctgccgcc      420
tgccccggtt ggttcctctg cacagcgatg gaagctgacc agcccgtcag cctcaccaat      480
atgcctgacg aaggcgtcat ggtcaccaaa ttctacttcc aggaggacga gtag            534
```

<210> SEQ ID NO 10
<211> LENGTH: 534
<212> TYPE: DNA
<213> ORGANISM: Artificial Sequence
<220> FEATURE:
<223> OTHER INFORMATION: Synthetic Polynucleotide

<400> SEQUENCE: 10

```
atggaaatct gcagaggcct gcggagccac ctgattaccc tgctgctgtt cctgttccac       60
agcgagacaa tctgccggcc cagcggccgg aagtccagca agatgcaggc cttccggatc      120
tgggacgtga accagaaaac cttctacctg cggaacaacc agctggtggc cggatacctg      180
cagggcccca acgtgaacct ggaagagaag atcgacgtgg tgcccatcga gccccacgcc      240
ctgtttctgg gcatccacgg cggcaagatg tgcctgagct gcgtgaagtc cggcgacgag      300
acaagactgc agctggaagc cgtgaacatc accgacctga gcgagaaccg gaagcaggac      360
aagagattcg ccttcatcag aagcgacagc ggccccacca ccagctttga gagcgccgcc      420
tgccccggct ggttcctgtg tacagccatg aagccgacc agcccgtgtc cctgacaaac       480
atgcccgacg agggcgtgat ggtcaccaag ttctattttc aagaagatga gtaa            534
```

<210> SEQ ID NO 11
<211> LENGTH: 540
<212> TYPE: DNA
<213> ORGANISM: Artificial Sequence
<220> FEATURE:
<223> OTHER INFORMATION: Synthetic Polynucleotide

<400> SEQUENCE: 11

```
gccaccatgg aaatctgcag aggcctgcgg agccacctga ttccctgct gctgttcctg       60 ttccacagcg agacaatctg ccggcccagc ggccggaagt ccagcaagat gcaggccttc      120
cggatctggg acgtgaacca gaaaaccttc tacctgcgga acaaccagct ggtggccgga      180
tacctgcagg gccccaacgt gaacctggaa gagaagatcg acgtggtgcc catcgagccc      240
cacgccctgt ttctgggcat ccacggcggc aagatgtgcc tgagctgcgt gaagtccggc      300
gacgagacaa gactgcagct ggaagccgtg aacatcaccg acctgagcga gaaccggaag      360
caggacaaga gattcgcctt catcagaagc gacagcggcc ccaccaccag ctttgagagc      420
gccgcctgcc ccggctggtt cctgtgtaca gccatggaag ccgaccagcc cgtgtccctg      480
acaaacatgc ccgacgaggg cgtgatggtc accaagttct attttcaaga agatgagtaa     540
```

IL-1RA CDNAS

RELATED APPLICATIONS

This application is a national stage filing under 35 U.S.C. § 371 of International Patent Application Serial No. PCT/US2017/065173, filed Dec. 7, 2017, entitled "IL-1RA CDNAS," by Ghivizzani, which claims the benefit of U.S. Provisional Application Ser. No. 62/431,336, filed on Dec. 7, 2016, entitled "IL-IRA CDNAS," by Ghivizzani, and U.S. Provisional Application Ser. No. 62/486,944, filed on Apr. 18, 2017, entitled "IL-1RA CDNAS," by Ghivizzani, each of which is incorporated herein by reference in its entirety.

GOVERNMENT SUPPORT

This invention was made with government support under AR048566; awarded by the National Institutes of Health. The government has certain rights in the invention.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Oct. 11, 2022, is named U119770099US02-SUBSEQ-COB and is 7,152 bytes in size.

BACKGROUND

Osteoarthritis (OA) is a degenerative, debilitating condition of weight bearing joints. The pathology of OA is marked by the gradual, persistent erosion of the articular cartilage, development of osteophytes at the joint margins, sclerotic growth of subchondral bone, synovitis and in many cases synovitis and joint effusion. OA is incurable, difficult to manage, and frequently advances to disabling joint failure. In horses, osteoarthritis is not only a problem for older individuals, but also younger horses.

SUMMARY

There is strong evidence that interleukin-1 (IL-1) serves as an intra-articular mediator of cartilage loss, pain and inflammation in large weight-bearing joint conditions, such as osteoarthritis (OA). Its natural inhibitor, the IL-1 receptor antagonist (IL-1Ra), holds promise as an effective treatment, but clinical application is hindered by difficulty achieving and maintaining effective concentrations if IL-1Ra intra-articularly by conventional drug delivery methods.

The present disclosure relates, at least in part, to the development of a codon-modified genes encoding equine IL-1Ra (eqIL-1Ra) and human IL-1Ra (hIL-1Ra) and the finding that intra-articular delivery of the codon-modified eqIL-1Ra encoding gene raises the steady state levels of eqIL-1Ra in synovial fluid significantly, e.g., more than 100-fold over background for a period of at least 6 months in equine subjects, and leads to reduced lameness, joint effusion and synovitis in an equine OA model. The codon-modified eqIL-1Ra encoding gene provides higher levels of expression of eqIL-1Ra compared to the native or endogenous gene, without any change in the amino acid sequence of the eqIL-1Ra protein. Similarly, IL-1Ra expression using codon-modified human IL-1Ra cDNA exceeded that from the native human IL-1Ra sequence by approximately 2-4 fold. This disclosure also relates to the finding that in striking contrast to healthy joints, transgene expression after treatment is much higher in diseased synovium, particularly so in regions with inflammation and synovitis, compared to normal or undiseased tissue. This phenomenon results in animals with the worst overall pathology producing the highest levels of IL-1Ra.

By delivering cDNA for IL-1Ra to cells resident in the joint tissues (e.g., in a human, a horse, or other animal), and providing for high levels of independent expression, the biosynthetic machinery of the modified cells is directed to overproduce and continuously secrete transgenic IL-1Ra protein into the synovial fluid and surrounding tissue. Thus, the diseased joint becomes an endogenous site of sustained, elevated IL-1Ra production, eliminating the need for repeated application of the protein, while providing the greatest concentration of the therapeutic specifically at the site of disease.

Accordingly, in some aspects, the present disclosure provides a recombinant nucleic acid comprising a codon-modified gene encoding IL-1Ra. In some embodiments, the IL-1Ra is equine. In some embodiments, the IL-1Ra is human. In some embodiments, the sequence of the codon-modified gene encoding equine IL-1Ra is of SEQ ID NO: 2. In some embodiments, the sequence of the codon-modified gene encoding human IL-1Ra is of SEQ ID NO: 10.

In some embodiments, a recombinant nucleic acid comprising a codon-modified gene encoding eqIL-1Ra or human IL-1Ra further comprises a Kozak sequence immediately upstream of the translation start site of the codon-modified gene. In some embodiments, the Kozak sequence and eq-IL-1Ra encoding gene is of sequence SEQ ID NO: 3. In some embodiments, the Kozak sequence and human IL-1Ra encoding gene is of sequence SEQ ID NO: 11. In some embodiments, the Kozak sequences further improve the expression level of human IL-1Ra (hIL-1Ra) or eqIL-1Ra in joints (e.g., in human joints or equine joints respectively).

In some embodiments, a recombinant nucleic acid comprising a codon-modified eqIL-1Ra or hIL-1Ra gene further comprises a promoter upstream of the codon-modified gene encoding eqIL-1Ra or hIL-1Ra. In some embodiments, a promoter is a cytomegalovirus (CMV) immediate early promoter/enhancer. In some embodiments, a CMV immediate early promoter/enhancer is of sequence SEQ ID NO: 4.

To deliver a codon-modified gene encoding IL-1Ra and ensure continuous expression of eqIL-1Ra protein in a joint over a long period of time, use of adeno-associated virus was considered. Accordingly, in some aspects, provided herein is a recombinant adeno-associated virus (rAAV) particle comprising any one of the nucleic acids disclosed herein. In some embodiments, the rAAV particle is self-complementary (i.e., a scAAV particle).

In some embodiments, the rAAV particle is of serotype 2.5. In some embodiments, the rAAV particle is of serotype 2. In some embodiments, a rAAV particle comprising a codon-modified eqIL-1Ra is AAV2.5. In some embodiments, a rAAV particle comprising a codon-modified hIL-1Ra is AAV2. In some embodiments, a rAAV particle comprising a codon-modified eqIL-1Ra is AAV2. In some embodiments, a rAAV particle comprising a codon-modified hIL-1Ra is AAV2.5.

In some aspects, provided herein is a method of treating a degenerative condition of large weight-bearing joints. The method comprises administering to a subject in need thereof any one of the rAAV particles disclosed herein. In some embodiments, a method of treating a degenerative condition of large weight-bearing joints comprises administering to a subject in need thereof an therapeutically effective amount of any one of the rAAV particles disclosed herein.

In some embodiments, a degenerative condition of large weight-bearing joints is osteoarthritis. In some embodiments, the subject is equine. In some embodiments, the subject is human. In some embodiments, any one of the rAAV particles disclosed herein is administered to a subject by intra-articular injection. In some embodiments, an equine subject is administered any one of the rAAV particles disclosed herein that comprise codon-modified equine IL-1Ra. In some embodiments, a human subject is administered any one of the rAAV particles disclosed herein that comprise codon-modified human IL-1Ra.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 1 shows sequence of the codon modified equine IL-1Ra cDNA. The sequence of the native equine IL-1Ra cDNA is shown on top (SEQ ID NO: 1), and the modified sequence at the bottom (SEQ ID NO: 2). The bases are numbered starting from the ATG of the translation initiation site to the translation termination codon. The nucleotide substitutions used for modification are indicated by colons. The sequence at the bottom indicates the Kozak consensus sequence (17) inserted immediately upstream from the translation start site. The modified sequence, including the Kozak consensus sequence, is SEQ ID NO: 3.

FIG. 2A shows eqIL-1Ra in conditioned media at 48 hours following transfection of equine synovial fibroblasts with the Hpa-trs-sk scAAV vector plasmid containing the coding sequences for GFP, native eqIL-1Ra, codon-modified eqIL-1Ra (Opt), and codon-modified eqIL-1Ra with a Kozak sequence leader (K+Opt). n=3 transfections. FIG. 2B shows eqIL-1Ra in conditioned media following infection of equine synovial fibroblasts with increasing doses of scAAV.eqIL-1Ra packaged in serotype 2.5. Viral genomes (vg) per cell for scAAV.eqIL-1Ra are shown to the right. Parallel infection with $10^5$ vg/cell of scAAV.GFP was used as a negative control. n=3 infections. FIG. 2C shows the anatomic locations of the intercarpal (IC) and metacarpophalangeal (MCP) joints on the equine forelimbs (arrowheads) (right). Radiographic image of the equine carpus, showing the intercarpal joint (arrow), the radiocarpal bone (RC) and the antebrachiocarpal joint (*). FIG. 2D shows eqIL-1Ra in synovial fluids of forelimb joints injected with either saline or scAAV.eqIL-1Ra at vg doses shown to the right of the respective plots (n=6 joints). Error bars represent ±SEM.

FIGS. 3A-3O show the locations and phenotypes of cells transduced by scAAV.GFP following intra-articular injection into healthy and OA joints. The intercarpal (IC) joints of 3 healthy horses and 3 with late stage naturally-occurring OA were injected with $5\times10^{12}$ vg of scAAV.GFP. Two weeks later, the joint tissues were collected and analyzed for fluorescence. The opposing articulating surfaces of representative healthy (FIG. 3A) and OA (FIG. 3B) intercarpal joints. Arrows in FIG. 3B indicate full thickness cartilage erosion; osteophyte growth (*). FIGS. 3C-3D show scAAV.GFP expression in the villous synovium of a healthy joint. FIGS. 3E-3F show GFP expression across the synovial surface of an OA joint. FIGS. 3C and 3E are from freshly harvested tissues at 10×; FIGS. 3D-3F are cross sections in paraffin at 20×. FIGS. 3G-3H show scAAV.GFP expression in fresh cartilage shaved from a healthy joint. FIG. 3I shows GFP activity in healthy cartilage shaving following 48 hours in explant culture. FIGS. 3J-3K show GFP activity in fresh cartilage shaved from an OA joint. FIG. 3L shows GFP activity in OA cartilage from region with visible erosion. (FIGS. 3G, 3I, 3J, 3L 10×; FIGS. 3H, 3K 20×). FIG. 3M shows GFP expression in cartilage clusters from an OA joint (paraffin section). FIG. 3N shows GFP activity in freshly harvested osteophyte tissue (10×). FIG. 3O shows representative GFP expression in fresh synovial tissue harvested from an antebrachiocarpal joint, immediately proximal to an intercarpal joint receiving scAAV.GFP. The images shown are a composite from the 6 animals in both groups. A wide range of exposure times was used to capture the varying fluorescence intensities at different magnifications in the fresh tissue samples of variable thickness and composition. The contrast and brightness of individual panels were adjusted linearly for uniformity of appearance and to reflect fluorescence intensities viewed by direct microscopy.

FIGS. 4A and 4B show GFP expression in inflamed synovial tissue by direct fluorescence microscopy of freshly harvested tissues. FIG. 4A is 5× and FIG. 4B is 20×. FIGS. 4C and 4D show GFP activity in OA cartilage from regions with visible erosion. Both are at 5× magnification. FIGS. 4E-4G show GFP activity in chondrocyte clusters. FIG. 4E shows direct fluorescence in fresh shavings (40×). FIGS. 4F and 4G are from paraffin sections (20× and 40×, respectively). In FIG. 4G, the chondrocytes in several clusters are shown changing morphology in association with the degradation of the surrounding matrix. FIG. 4H shows GFP expression in fresh osteophyte tissue (20×).

FIGS. 5A-5G show intra-articular scAAV.eqIL-1Ra gene delivery and expression in an equine OCF model of OA. FIG. 5A is a schematic representation of the Osteochondral Fragment (OCF) efficacy study. A total of 20 horses were divided equally into two groups. Following surgical generation of an osteochondral lesion in the radial carpal bone, the animals in the Treated group received an injection of $5\times10^{12}$ vg of scAAV.eqIL-1Ra into the joint space; Control animals received an equal volume of saline. Synovial fluids from both intercarpal joints, peripheral blood, and urine were collected on alternate weeks (*). FIG. 5B shows the mean eqIL-1Ra levels in synovial fluid of the OCF joints from the Treated and Control groups. Dashed line reflects mean AAV.eqIL-1Ra expression in healthy joints from the same viral dose (see FIG. 5C) (n=10). FIG. 5C is a graph depicting the synovial fluid eqIL-1Ra in the OCF joint of each individual in the Treated group. Each line reflects a different animal. FIG. 5D shows the mean eqIL-1Ra in urine for both the Treated and Control groups (n=10). FIG. 5E shows the mean eqIL-1Ra in serum from peripheral blood for 9 of 10 animals in both the Treated and Control groups. FIG. 5F shows the eqIL-1Ra in blood serum from the remaining horses in both the Treated and Control groups, which were >25× greater than the other 18 animals in the study prior to treatment. FIG. 5G shows AAV2.5 neutralizing antibody titers in peripheral blood serum and synovial fluids of the OCF joints injected with scAAV.eqIL-1Ra (n=10). Error bars represent ±SEM.

FIG. 6A shows the relative change in mean visual lameness scores between Treated and Control groups during athletic training (left). Relative change in forelimb lameness (vector sum) from the Lameness Locator® inertial sensor motion analysis system (right). For both, mean lameness scores at week 1 were assigned a value of 1. FIG. 6B shows the mean $PGE_2$ levels in synovial fluid of OCF joints of both the Treated and Control groups. Error bars represent ±SEM; *P<0.05.

FIG. 7A shows representative images from axial and sagittal scans (PD and PD-FS, respectively) of OCF joints from one horse in the Treated and Control groups. White arrows indicate: CE-capsular effusion; ME— marrow edema; OCF— osteochondral fragment; SE—synovial effusion. Black arrow in Week 12 sagittal scan for the control joint indicates hyperintense signal and incomplete OCF repair. FIG. 7B shows covariate analyses of the major joint pathologies associated with the OCF model in Treated and Control groups at endpoint (Week 12) using the pre-treatment scores (Week 0) as baselines (left). Total MRI scores for the OCF joints were calculated from the values of the individual MRI pathologies (right, cross-hatch). Total MRI scores from Sham operated joints represent baseline pathology levels in opposing intercarpal joints. Error bars represent ±SEM; *P<0.05.

FIGS. 8A-8D show an evaluation of OCF joint arthroscopies and histologic sections for changes in tissue pathology associated with scAAV.eqIL-1Ra treatment. Both intercarpal joints of the horses in the Treated and Control groups were examined arthroscopically following generation of the osteochondral lesion (Week −2) and at endpoint (Week 12). Images were scored for OCF size and local cartilage damage, synovitis, cartilage damage throughout the joint (overall) and ligament inflammation. At endpoint, the osteochondral fragment and regional synovial tissue were removed, sectioned and stained with H&E or toluidine blue and graded. FIG. 8A shows covariate analyses of arthroscopic assessments of the major joint pathologies associated with the OCF model in Treated and Control groups at Week 12 using the scores at Week −2 as baseline (left). Total arthroscopy scores for the OCF joints were calculated from the values of the individual pathologies (right, cross-hatched bars). Total scores from Sham operated opposing intercarpal joints represent baseline pathology in uninjured joints. FIG. 8B presents representative arthroscopic images of the osteochondral lesions in Treated and Control horses at the time of generation (Week −2) and at endpoint (Week 12). FIG. 8C shows the mean histologic scores for individual tissue pathologies in collected OCF tissues (left). Total histologic scores calculated from the individual tissue scores (right). FIG. 8D shows representative microscopic images of bone repair tissue in Treated and Controls. Error bars represent ±SEM; *P<0.05.

FIG. 9A shows plots of total MRI score in the Treated horses immediately prior to scAAV.eqIL-1Ra injection vs OCF synovial fluid eqIL-1Ra levels at week 2 (left) and mean eqIL-1Ra levels from weeks 2-12 (right). For both plots, the arrow designates the data point from one horse with unusually high eqIL-1Ra expression at week 2 relative to the other 9 animals (see FIG. 5C). The solid lines show the best fit line plots for the data points of all 10 animals. The dashed lines show the best fit line plots calculated without the outlying data point. Pearson correlation coefficients (r) for MRI score and eqIL-1Ra level both with (All) and excluding the outlying data point (9/10) are shown. FIG. 9B is a plot of total MRI scores immediately prior to injection versus total MRI score at endpoint for the OCF joints for each of the horses in the Treated (gray) and Control (black) groups. The solid lines show the best fit line plots for each group. The corresponding line equations and Pearson correlation coefficients are also shown. *P<0.05.

FIG. 10 shows secretion of human IL-1Ra in HEK293 cells transfected with scAAV vector plasmids containing native or codon-modified human IL-1Ra cDNA.

FIG. 13 shows alignment of the sequences of the native human IL-1Ra cDNA (top sequence; SEQ ID NO: 9) and the GeneArt codon modified IL-1Ra sequence (bottom sequence; SEQ ID NO: 10) with consensus Kozak sequence (underlined) immediately upstream of the ATG translation start site at position 1. Differences between the two sequences are indicated by colons. As indicated beneath the sequence alignments, 105 of the 534 nucleotides in the native IL-1Ra cDNA sequence were changed in the modification. The modified sequence, including the Kozak consensus sequence, is SEQ ID NO: 11.

DETAILED DESCRIPTION

Figure 2B:
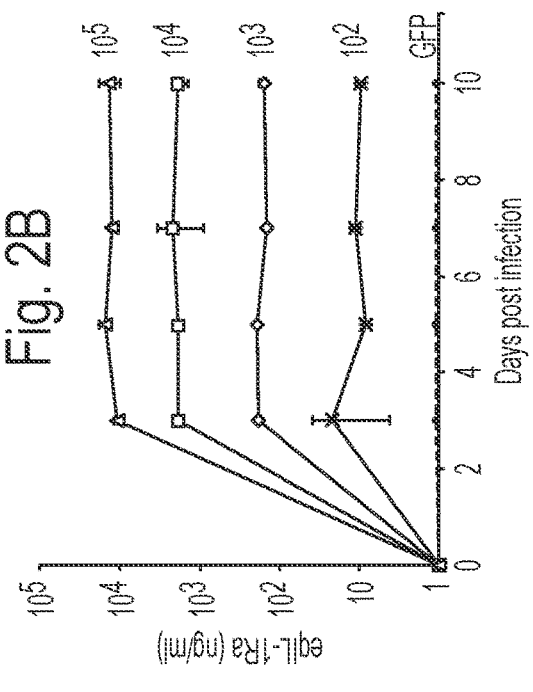
FIGS. 2A-2D show the expression of the eqIL-1Ra transgene in vitro and in vivo.

Il-1Ra is a promising therapeutic for diseases of degenerative condition of large weight-bearing joints such as osteoarthritis (OA) since it is a natural antagonist of IL-1, which is implicated in intra-articular cartilage loss, pain and inflammation. However, delivering IL-1Ra to the site of disease, i.e., the joints, is challenging. Sustaining a therapeutically effective level of IL-1Ra in a diseased joint for a long period of time is even more challenging. Indeed in horses, endogenous IL-1Ra is expressed at low levels. In fact, exogenous expression of IL-1Ra using the wild-type nucleotide sequence that encodes eqIL-1Ra protein also does not aid in achieving high levels of IL-Ra in joints.

As a solution to this problem, the inventors of this disclosure developed a codon-modified nucleic acid sequence that encodes eqIL-1Ra that has the same amino acid sequence as wild-type eqIL-1Ra protein, but results in higher exogenous expression levels of IL-1Ra. A further modification was made to include a Kozak sequence immediately upstream of the translation start site. Inclusion of this Kozak sequence further improves the level of expression of eqIL-1Ra protein. Delivery of the developed codon-modified IL-1Ra encoding gene to joints was achieved by use of AAV particles as carriers. Surprisingly, it was found that there is a strong correlation between the level of pathology in a joint at the time of injection and downstream IL-1Ra production. Surprisingly, diseased tissue expresses higher levels of eqIL-1Ra by the disclosed treatment method than tissue that is not diseased.

The inventors also developed codon-modified human IL-1Ra (hIL-1Ra) with and without Kozak leader sequences that result in secretion of IL-1Ra at levels that are approximately 2-4 times higher than that by native hIL-1Ra cDNA.

Nucleic Acid Comprising a Codon-Modified Gene Encoding Equine IL-1Ra

Provided herein is a recombinant nucleic acid comprising a codon-modified gene encoding equine IL-1Ra (eqIL-1Ra). In some embodiments, the nucleotide sequence mismatch between an eqIL-1Ra encoding codon-modified gene and the endogenous (or wild-type or native) eqIL-1Ra encoding gene is 10-30% (e.g., 15-25%, 17-23%, 19-21%, 10-15%, 15-20% 20-25% or 25-30%). That is, 10-30% of the nucleotides encoding eqIL-1Ra are codon-modified. In some embodiments, the eqIL-1Ra encoding codon-modified gene has 20.2% mismatch compared to the wild-type eqIL-1Ra encoding gene. SEQ ID NO: 1 provides the nucleotide sequence of wild-type eqIL-1Ra encoding gene. SEQ ID NO:2 provides a codon-modified sequence encoding eqIL-1Ra. 108 out of 534 nucleotides of SEQ ID NO: 2 are mismatched compared to SEQ ID NO: 1, which corresponds to a mismatch of 20.2% (FIG. 1).

Nucleotide Sequence of Endogenous eqIL-1Ra Encoding Gene:

```
                                           (SEQ ID NO: 1)
ATGGAAATCCGCAGGCGTTCTGTCAGACACCTAATCTCTCTCCTCCTTTT

CTTGTTCTACTCAGAGACAGCCTGCCACCCTTTGGGGAAGAGACCCTGCA

AGATGCAAGCCTTCAGAATCTGGGATGTTAACCAGAAGACCTTCTACATG

AGGAATAACCAACTAGTTGCTGGATACTTGCAAGAATCAAATACTAAATT

ACAAGAGAAGATAGATGTGGTGCCCATTGAGCCTGATGCTCTATTCCTGG

GACTCCATGGGAGGAAGCTGTGCCTGGCCTGTGTCAAGTCTGGTGATGAG

ATTAGGTTCCAATTGGAGGCAGTTAACATCACTGACCTGAGCAAGAACAA

GGAGGAGAACAAGCGCTTCACCTTCATCCGCTCAAACAGTGGCCCCACCA

CCAGCTTCGAGTCTGCCGCCTGCCCTGGCTGGTTCCTCTGCACGGCGCAG

GAGGCAGACCGGCCCGTCAGCCTCACCAACAAGCCCAAAGAGTCCTTCAT

GGTCACCAAGTTCTACCTCCAGGAGGACCAGTAG
```

Example of Nucleotide Sequence of Codon-Modified eqIL-1Ra Encoding Gene:

```
                                           (SEQ ID NO: 2)
ATGGAAATCAGGCGCAGAAGCGTGCGCCACCTGATCAGCCTGCTGCTGTT

CCTGTTCTACAGCGAGACAGCCTGCCACCCCCTGGGCAAGAGGCCCTGCA

AGATGCAGGCCTTCAGGATCTGGGACGTGAACCAGAAAACCTTCTACATG

CGCAACAACCAGCTGGTGGCCGGATACCTGCAGGAAAGCAACACCAAGCT

GCAGGAAAAGATCGACGTCGTCCCCATCGACCCGACGCCCTGTTCCTGGG

CCTGCACGGCAGAAAGCTGTGCCTGGCCTGCGTGAAGTCCGGCGACGAGA
```

TCAGGTTTCAGCTGGAAGCCGTGAACATCACCGACCTGAGCAAGAACAAA

GAGGAAAACAAGCGCTTCACCTTCATCAGAAGCAACAGCGGCCCCACCAC

CAGCTTCGAGAGCGCCGCTTGCCCCGGCTGGTTCCTGTGTACAGCCCAGG

AAGCCGACAGGCCCGTCAGCCTGACCAACAAGCCCAAAGAAAGCTTCATG

GTCACCAAGTTCTATCTGCAAGAAGATCAGTAA

In some embodiments, transduction of a cell with a codon-modified eqIL-1Ra encoding gene results in eqIL-1Ra protein levels that are 5-200 fold higher (e.g., 5-200, 10-150, 15-120, 20-100, 30-80, 35-60, 40-50 fold higher) compared to when a similar cell is transduced with endogenous (or native or wild-type) eqIL-1Ra encoding gene. A wild-type eqIL-1Ra encoding gene is one that is native or endogenous, or found in horses.

Kozak Sequence

In some embodiments, a codon-modified eqIL-1Ra encoding gene is preceded by a Kozak sequence. In some embodiments, a Kozak sequence immediately precedes the translation start site of a codon-modified eqIL-1Ra encoding gene. In some embodiments, a Kozak sequence is 1-50 nucleotides upstream from the translation start site of a codon-modified eqIL-1Ra encoding gene. In some embodiments, a Kozak sequence is GCCACC. SEQ ID NO: 3 provides an example of a codon-modified eqIL-1Ra encoding gene that is immediately preceded by a Kozak sequence.

Example of Nucleotide Sequence of Codon-Modified eqIL-1Ra Encoding Gene (Kozak Sequence is Underlined):

```
                                           (SEQ ID NO: 3)
GCCACCATGGAAATCAGGCGCAGAAGCGTGCGCCACCTGATCAGCCTGCT

GCTGTTCCTGTTCTACAGCGAGACAGCCTGCCACCCCCTGGGCAAGAGGC

CCTGCAAGATGCAGGCCTTCAGGATCTGGGACGTGAACCAGAAAACCTTC

TACATGCGCAACAACCAGCTGGTGGCCGGATACCTGCAGGAAAGCAACAC

CAAGCTGCAGGAAAAGATCGACGTCGTCCCCATCGACCCGACGCCCTGTT

CCTGGGCCTGCACGGCAGAAAGCTGTGCCTGGCCTGCGTGAAGTCCGGCG

ACGAGATCAGGTTTCAGCTGGAAGCCGTGAACATCACCGACCTGAGCAAG

AACAAAGAGGAAAACAAGCGCTTCACCTTCATCAGAAGCAACAGCGGCCC

CACCACCAGCTTCGAGAGCGCCGCTTGCCCCGGCTGGTTCCTGTGTACAG

CCCAGGAAGCCGACAGGCCCGTCAGCCTGACCAACAAGCCCAAAGAAAGC

TTCATGGTCACCAAGTTCTATCTGCAAGAAGATCAGTAA
```

In some embodiments, transduction of a cell with a codon-modified eqIL-1Ra encoding gene with a Kozak sequence results in eqIL-1Ra protein levels that are 5-200 fold higher (e.g., 5-200, 10-150, 15-120, 20-100, 30-80, 35-60, 40-50 fold higher) compared to when a similar cell is transduced with endogenous eqIL-1Ra encoding gene. A similar cell is one that has the same genetic make-up and is cultured and treated in the same manner except that one variable effecting the cell is different, e.g., the sequence of the IL-1Ra cDNA that is used to transfect it.

Nucleic Acid Comprising a Codon-Modified Gene Encoding Human IL-1Ra

Contemplated herein are also recombinant nucleic acids comprising a codon-modified gene encoding human IL-1Ra. In some embodiments, the nucleotide sequence mismatch between an human IL-1Ra encoding codon-modified gene and the endogenous (or wild-type or native) human IL-1Ra encoding gene is 10-30% (e.g., 15-25%, 17-23%, 19-21%, 10-15%, 15-20% 20-25% or 25-30%). That is, 10-30% of the nucleotides encoding human IL-1Ra are codon-modified. In some embodiments, the human IL-1Ra encoding codon-modified gene has 19.6% mismatch compared to the wild-type human IL-1Ra encoding gene. SEQ ID NO: 9 provides the nucleotide sequence of wild-type human IL-1Ra encoding gene. SEQ ID NO:10 provides an example of a codon-modified sequence encoding human IL-1Ra. 105 out of 534 nucleotides of SEQ ID NO: 10 are mismatched compared to SEQ ID NO: 9, which corresponds to a mismatch of 19.6% (see FIG. 13).

Example of Nucleotide Sequence of Endogenous Human IL-1Ra Encoding Gene:

(SEQ ID NO: 9)
ATGGAAATCTGCAGAGGCCTCCGCAGTCACCTAATCACTCTCCTCCTCTT

CCTGTTCCATTCAGAGACGATCTGCCGACCCTCTGGGAGAAAATCCAGCA

AGATGCAAGCCTTCAGAATCTGGGATGTTAACCAGAAGACCTTCTATCTG

AGGAACAACCAACTAGTTGCTGGATACTTGCAAGGACCAAATGTCAATTT

AGAAGAAAGATAGATGTGGTACCCATTGAGCCTCATGCTCTGTTCTTGG

GAATCCATGGAGGGAAGATGTGCCTGTCCTGTGTCAAGTCTGGTGATGAG

ACCAGACTCCAGCTGGAGGCAGTTAACATCACTGACCTGAGCGAGAACAG

AAAGCAGGACAAGCGCTTCGCCTTCATCCGCTCAGACAGTGGCCCCACCA

CCAGTTTTGAGTCTGCCGCCTGCCCCGGTTGGTTCCTCTGCACAGCGATG

GAAGCTGACCAGCCCGTCAGCCTCACCAATATGCCTGACGAAGGCGTCAT

GGTCACCAAATTCTACTTCCAGGAGGACGAGTAG

Example of a Nucleotide Sequence of Codon-Modified Human IL-1Ra Encoding Gene:

(SEQ ID NO: 10)
ATGGAAATCTGCAGAGGCCTGCGGAGCCACCTGATTACCCTGCTGCTGTT

CCTGTTCCACAGCGAGACAATCTGCCGGCCCAGCGGCCGGAAGTCCAGCA

AGATGCAGGCCTTCCGGATCTGGGACGTGAACCAGAAAACCTTCTACCTG

CGGAACAACCAGCTGGTGGCCGGATACCTGCAGGGCCCCAACGTGAACCT

GGAAGAGAAGATCGACGTGGTGCCCATCGAGCCCACGCCCTGTTTCTGG

GCATCCACGGCGGCAAGATGTGCCTGAGCTGCGTGAAGTCCGGCGACGAG

ACAAGACTGCAGCTGGAAGCCGTGAACATCACCGACCTGAGCGAGAACCG

GAAGCAGGACAAGAGATTCGCCTTCATCGAAGCGACAGCGGCCCCACCA

CCAGCTTTGAGAGCGCCGCCTGCCCCGGCTGGTTCCTGTGTACAGCCATG

GAAGCCGACCAGCCCGTGTCCCTGACAAACATGCCCGACGAGGGCGTGAT

GGTCACCAAGTTCTATTTTCAAGAAGATGAGTAA

In some embodiments, a codon-modified human IL-1Ra encoding gene is preceded by a Kozak sequence. In some embodiments, a Kozak sequence immediately precedes the translation start site of a codon-modified human IL-1Ra encoding gene. In some embodiments, a Kozak sequence is 1-50 nucleotides upstream from the translation start site of a codon-modified human IL-1Ra encoding gene. In some embodiments, a Kozak sequence is GCCACC. SEQ ID NO: 11 provides an example of a codon-modified human IL-1Ra encoding gene that is immediately preceded by a Kozak sequence.

Example of Nucleotide Sequence of Codon-Modified Human IL-1Ra Encoding Gene (Kozak Sequence is Underlined):

(SEQ ID NO: 11)
<u>GCCACC</u>ATGGAAATCTGCAGAGGCCTGCGGAGCCACCTGATTACCCTGCT

GCTGTTCCTGTTCCACAGCGAGACAATCTGCCGGCCCAGCGGCCGGAAGT

CCAGCAAGATGCAGGCCTTCCGGATCTGGGACGTGAACCAGAAAACCTTC

TACCTGCGGAACAACCAGCTGGTGGCCGGATACCTGCAGGGCCCCAACGT

GAACCTGGAAGAGAAGATCGACGTGGTGCCCATCGAGCCCACGCCCTGT

TTCTGGGCATCCACGGCGGCAAGATGTGCCTGAGCTGCGTGAAGTCCGGC

GACGAGACAAGACTGCAGCTGGAAGCCGTGAACATCACCGACCTGAGCGA

GAACCGGAAGCAGGACAAGAGATTCGCCTTCATCAGAAGCGACAGCGGCC

CCACCACCAGCTTTGAGAGCGCCGCCTGCCCCGGCTGGTTCCTGTGTACA

GCCATGGAAGCCGACCAGCCCGTGTCCCTGACAAACATGCCCGACGAGGG

CGTGATGGTCACCAAGTTCTATTTTCAAGAAGATGAGTAA

In some embodiments, transduction of a cell with a codon-modified human IL-1Ra encoding gene with a Kozak sequence results in human IL-1Ra protein levels that are 1.1-50 fold higher (e.g., 1.1-3, 1.4-10, 1.5-30, 2-30, 2-50, 2-4, 2.5-5, 3-8, 5-20 or 30-15 fold higher) compared to when a similar cell is transduced with endogenous human IL-1Ra encoding gene.

Promoter

A promoter, generally, is a region of nucleic acid that initiates transcription of a nucleic acid encoding a product.

To achieve exogenous expression levels of eqIL-1Ra or hIL-1Ra, any of a number of promoters may be employed. The promoter may be, for example, a constitutive promoter, tissue-specific promoter, inducible promoter, or a synthetic promoter.

A recombinant nucleic acid as described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and cytomegalovirus (CMV) immediate early promoter/enhancer. Non-limiting examples of other constitutive mammalian promoters include various housekeeping gene promoters, as exemplified by the β-actin promoter (e.g., chicken β-actin promoter) and human elongation factor-1 α (EF-1α) promoter.

In some embodiments, a promoter in any one of the recombinant nucleic acids disclosed herein is a disease-controlled promoter. A disease-controlled promoter is one which allows expression of Il-1Ra encoded by the codon-modified gene to which the promoter is linked in diseased cells or tissue at levels that are higher than those in undiseased cells or tissue. In some embodiments, a disease-controlled promoter in any one of the recombinant nucleic acids disclosed herein is a cytomegalovirus (CMV) immediate early promoter/enhancer. In some embodiments, inclusion of a CMV immediate early promoter/enhancer results in 1.5 to 200 fold higher (e.g., 1.5-150, 2-120, 5-100, 10-80 or 20-50 fold higher) eqIL-1Ra or hIL-1Ra expression levels in diseased tissue compared to undiseased tissue. In some embodiments, the diseased and undiseased tissue is in the same joint of a subject. In some embodiments, the diseased and undiseased tissue are in the same subject but in different joints. In some embodiments, diseased and undiseased tissue are in different subjects. Sequence of the CMV immediate early promoter/enhancer is known in the art and is discussed by Schmidt et al. (Molecular and Cellular Biol., 1990, 10:4406).

In some embodiments, the sequence of a CMV immediate early promoter/enhancer is SEQ ID NO: 4. In some embodiments, the sequence of a CMV immediate early promoter/enhancer is a portion of SEQ ID NO: 4 such that the portion provides 20-50% (e.g., 20, 30, 40, 50, 60, 70, 80, 90, 95, 99 or 100%) activity of SEQ ID NO: 4.

Example of CMV Immediate Early Promoter/Enhancer Nucleotide Sequence

```
                                            (SEQ ID NO: 4)
TCAATATTGGCCATTAGCCATATTATTCATTGGTTATATAGCATAAATCA

ATATTGGCTATTGGCCATTGCATACGTTGTATCTATATCATAATATGTAC

ATTTATATTGGCTCATGTCCAATATGACCGCCATGTTGGCATTGATTATT

GACTAGTTATTAATAGTAATCAATTACGGGGTCATTAGTTCATAGCCCAT

ATATGGAGTTCCGCGTTACATAACTTACGGTAAATGGCCCGCCTGGCTGA

CCGCCCAACGACCCCCGCCCATTGACGTCAATAATGACGTATGTTCCCAT

AGTAACGCCAATAGGGACTTTCCATTGACGTCAATGGGTGGAGTATTTAC

GGTAAACTGCCCACTTGGCAGTACATCAAGTGTATCATATGCCAAGTCCG

CCCCCTATTGACGTCAATGACGGTAAATGGCCCGCCTGGCATTATGCCCA

GTACATGACCTTACGGGACTTTCCTACTTGGCAGTACATCTACGTATTAG

TCATCGCTATTACCATGGTGATGCGGTTTTGGCAGTACACCAATGGGCGT

GGATAGCGGTTTGACTCACGGGGATTTCCAAGTCTCCACCCCATTGACGT

CAATGGGAGTTTGTTTTGGCACCAAAATCAACGGGACTTTCCAAAATGTC

GTAACAACTGCGATCGCCCGCCCCGTTGACGCAAATGGGCGGTAGGCGTG

TACGGTGGGAGGTCTATATAAGCAGAGCTCGTTTAGTGAACCGTCAGATC
```

A promoter may be located upstream (e.g., 0 bp to −100 bp, −30 bp, −75 bp, or −90 bp) from the transcriptional start site of a nucleic acid encoding a product, or a translation start site may be located within a promoter. In some embodiments, a promoter is located immediately upstream of a Kozak sequence, or up to 90 bp upstream of a Kozak sequence. A promoter may have a length of 100-1000 nucleotide base pairs, or 50-2000 nucleotide base pairs.

rAAV for Delivery of eqIL-1Ra or Human IL-1Ra

As a vehicle for delivering the eqIL-1Ra or human IL-1Ra encoding transgene, recombinant adeno-associated (rAAV) particles are used. AAV has emerged as one of the most favorable vehicle for gene therapy in clinical applications. Its benefits are related to its increased safety, the low immunogenic profile of transduced cells, and its ability to provide prolonged, effective transgene expression in joint tissues. Recent advances in AAV technology, including the development of self-complementary (double-stranded) vectors, and improved methods for high-titer vector production, have further increased its potential for mainstream clinical use.

In some embodiments, the serotype of the rAAV particle used to deliver any one of the nucleic acids disclosed herein to an equine or human joint is serotype 2. In some embodiments, the serotype of the rAAV particle used to deliver any one of the nucleic acids disclosed herein to an equine or human joint is serotype 2.5 and is self-complementary (scAAV2.5). scAAV2.5 is a second generation AAV vector that includes development of both a novel capsid sequence (chimeric) and unique vector genome structure (duplexed). The hybrid AAV serotype 2.5 shows the same tissue tropism as serotype 2, but shows reduced reactivity with AAV2 neutralizing antibody. In some embodiments, the serotype of the rAAV particle used to deliver any one of the nucleic acids disclosed herein to an equine or human joint is serotype 1, 2, 3, 4, 5, 6, 7, 8, 9, 10, 11, 12, 13, any hybrid serotype, or modified or engineered AAV capsid.

In some embodiments, a rAAV particle is self-complimentary, in that it contains a region of the nucleic acid that is complementary to another region of the nucleic acid, initiating the formation of the double-strandedness of the nucleic acid comprised in a particle.

In some embodiments, a high capacity adenovirus vector is used as a vehicle for delivering any one of the eqIL-1Ra or human IL-1Ra encoding transgenes disclosed herein.

It is to be understood that other gene delivery vehicles, e.g., lentivirus, can also be used as a vehicle for delivering any one of the eqIL-1Ra or human IL-1Ra encoding transgenes disclosed herein. Various gene delivery methods are known in the art, see e.g., Nayerossadat et al. (Adv Biomed Res. 2012; 1: 27), which is incorporated herein by reference in its entirety, and can be used as a vehicle for delivering any one of the eqIL-1Ra or human IL-1Ra encoding transgenes disclosed herein.

Methods of Packaging rAAV Particles

Non-limiting methods of producing rAAV particles that comprise nucleic acid comprising codon-modified gene encoding eqIL-1Ra or human IL-1Ra are described herein. Other methods are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; Li et al., J. Virol, 2012, v.86(15) and plasmids and kits available from ATCC and Cell Biolabs, Inc.). For example, a plasmid comprising a codon-modified eqIL-1Ra or human IL-1Ra encoding gene may be combined with one or more helper plasmids, e.g., that contain a rep gene (e.g., encoding Rep78, Rep68, Rep52 and Rep40) and a cap gene (encoding VP1, VP2, and VP3, including a modified VP2 region as described herein), and transfected into recombinant cells such that the rAAV particle can be packaged and subsequently purified.

In some embodiments, packaging is performed in a helper cell or producer cell, such as a mammalian cell or an insect cell. Non-limiting examples of mammalian cells include, but are not limited to, HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). Exemplary insect cells include, but are not limited to Sf9 cells (see, e.g., ATCC® CRL-1711™). The helper cell may comprises rep and/or cap genes that encode the Rep protein and/or Cap proteins for use in a method described herein. In some embodiments, the packaging is performed in vitro.

In some embodiments, a plasmid comprising an IL-1Ra encoding gene is combined with one or more helper plasmids, e.g., that contain a rep gene of a first serotype and a cap gene of the same serotype or a different serotype, and transfected into helper cells such that the rAAV particle is packaged.

In some embodiments, the one or more helper plasmids include a first helper plasmid comprising a rep gene and a cap gene, and a second helper plasmid comprising one or more of the following helper genes: E1a gene, E1b gene, E4 gene, E2a gene, and VA gene. For clarity, helper genes are genes that encode helper proteins E1a, E1b, E4, E2a, and VA. In some embodiments, the rep gene is a rep gene derived from AAV3, AAV5, or AAV6 and the cap gene is derived from AAV2, AAV3, AAV5, or AAV6 and may include modifications to the gene in order to produce the modified capsid protein described herein. In some embodiments, the cap gene is modified such that one or more of the proteins VP1, VP2 and VP3 do not get expressed. In some embodiments, the cap gene is modified such that VP2 does not get expressed. Methods for making such modifications are known in the art (Lux et al. (2005), J Virology, 79: 11776-87) Helper plasmids, and methods of making such plasmids, are known in the art and commercially available (see, e.g., pDF6, pRep, pDM, pDG, pDP1rs, pDP2rs, pDP3rs, pDP4rs, pDP5rs, pDP6rs, pDG (R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adeno associated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188). Plasmids that encode wild-type AAV coding regions for specific serotypes are also known and available. For example pSub201 is a plasmid that comprises the coding regions of the wild-type AAV2 genome (Samulski et al. (1987), J Virology, 6:3096-3101).

An exemplary, non-limiting, rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. In some embodiments, the one or more helper plasmids comprise rep genes for a first serotype (e.g., AAV3, AAV5, and AAV6), cap genes (which may or may not be of the first serotype) and optionally one or more of the adenoviral VA, E2A (DBP), and E4 genes under the transcriptional control of their native promoters. In some embodiments, the one or more helper plasmids comprise cap ORFs (and optionally rep ORFs) for the desired AAV serotype and the adenoviral VA, E2A (DBP), and E4 genes under the transcriptional control of their native promoters. The cap ORF may also comprise one or more modifications to produce a modified capsid protein as described herein. HEK293 cells (available from ATCC®) are transfected via CaPO$_4$-mediated transfection, lipids or polymeric molecules such as Polyethylenimine (PEI) with the helper plasmid(s) and a plasmid containing a nucleic acid vector described herein. The HEK293 cells are then incubated for at least 60 hours to allow for rAAV particle production. Alternatively, the HEK293 cells are transfected via methods described above with AAV-ITR containing any one of the recombinant nucleic acids described herein, a helper plasmid comprising genes encoding Rep and Cap proteins, and co-infected with a helper virus. Helper viruses are viruses that allow the replication of AAV. Examples of helper virus are adenovirus and herpesvirus.

Alternatively, in another example Sf9-based producer stable cell lines are infected with a single recombinant baculovirus containing any one of the recombinant nucleic acids provided herein. As a further alternative, in another example HEK293 or BHK cell lines are infected with a HSV containing the nucleic acid vector and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known in the art or described herein, e.g., by iodixanol step gradient, CsCl gradient, chromatography, or polyethylene glycol (PEG) precipitation.

Pharmaceutical Compositions

Provided herein is a pharmaceutical composition comprising any one of the rAAV particles disclosed herein. In some embodiments, a pharmaceutical composition comprises a pharmaceutically acceptable carrier that aids in the delivery of rAAV particles comprising a nucleic acid encoding eqIL-1Ra or human IL-1Ra to a joint of a subject. The term "carrier" refers to a diluent, adjuvant, excipient, or vehicle with which the rAAV particle is administered.

Pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions (e.g., sterilized, pyrogen-free saline) and aqueous dextrose and glycerol solutions can also be employed as liquid carriers. USP grade carriers and excipients are particularly useful for delivery of rAAV particles to mammalian subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, 22nd edition, Pharmaceutical Press, 2012.

The pharmaceutical forms of the rAAV particle compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. In some embodiments, the form is sterile. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

For administration of an injectable aqueous solution, the solution may be suitably buffered, if necessary, and the liquid diluent first rendered isotonic with sufficient saline or glucose. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for mammalian administration, preparations should meet sterility, pyrogenicity, and the general safety and purity standards generally accepted in veterinary sciences.

Typically, such compositions may contain at least about 0.1% of the therapeutic agent (e.g., rAAV particle) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Method of Treatment

Provided herein is a method of treating a degenerative condition of large weight-bearing joints, the method comprising administering intra-articularly to a subject any one of the rAAV particles disclosed herein.

In some embodiments, a subject is mammalian (e.g., a human or a horse). In some embodiments, the subject is equine. In some embodiments, the subject is human.

In some embodiments, a degenerative condition of large weight-bearing joints is caused by acute trauma (e.g., injury or traumatic loading) or chronic erosive disease. In some embodiments, a degenerative condition of large weight-bearing joints is osteoarthritis (OA). Equine OA is also known as degenerative joint disease (DJD). OA in horses can be caused by trauma to the joint from either an acute incident or constant concussive forces. Immobilization and improper shoeing can also lead to OA in horses.

In some embodiments, any one of the rAAV particles or pharmaceutical compositions is administered in joint needing treatment by intra-articular injection. The joints most often affected by arthritis and thus in need of treatment in horses include the knee, fetlock, coffin, hock, and pastern (where it is often referred to as "ringbone"). In some embodiments, the joint needing treatment is a metacarpophalangeal (MCP) or intercarpal (IC) joint. Accordingly, in some embodiments, a recombinant gene (e.g., in an rAAV) is delivered directly (e.g., injected) to one of these joints. However, in some embodiments, a composition may be delivered systemically.

It is to be understood that any one of the rAAV particles described herein can be used to treat any pathologic condition where sustained production of an IL-1 inhibitor would provide benefit. In some embodiments, a pathologic condition where sustained production of IL-1 inhibitor would provide benefit is gout, pseudo-gout, or the pain and inflammation associated with gout or pseudo gout. Other non-limiting examples of pathologic conditions where sustained production of IL-1 inhibitor would provide benefit include rheumatoid arthritis, juvenile arthritis, still's disease, polyarthritis, chronic infantile neurological cutaneous and articular syndrome, vasculitis, systemic lupus erythematosus, psoriatic arthropathy, connective tissue disorder, immune reconstitution syndrome, diffuse vasculitis, schnitzler's syndrome, amyloidosis, histiocytosis haematophagic, muckle-wells syndrome, osteoporosis, polychondritis, ocular hypertension, ankylosing spondylitis, erdheim-chester disease, crush injury, sapho syndrome, multiple injuries, cytolytic hepatitis, scleroderma, amyotrophic lateral sclerosis, tumour necrosis factor receptor-associated periodic syndrome, antiinflammatory therapy, autoimmune disorder, ill-defined disorder, bone marrow disorder, psoriasis, immune system disorder, castleman's disease, pyrexia, interferon gamma receptor deficiency, cryopyrin associated periodic syndrome, dermatomyositis, sjogren's syndrome, urticaria thermal, polymyalgia rheumatica, blood immunoglobulin d increased, breast cancer, inflammation, and reiter's syndrome. In some embodiments, a method of treating a pathologic condition where sustained production of IL-1 inhibitor (e.g., gout or pseudo-gout) would provide benefit comprises administering to a subject in need thereof any one of the rAAV particles disclosed herein intra-articularly. In some embodiments, a method of treating a pathologic condition comprises administering to a subject in need thereof any one of the rAAV particles disclosed herein extra-articularly.

In some embodiments, any one of the rAAV particles described herein is used to treat a persistent inflammatory condition (e.g., an inflammatory condition in connective tissues). In some embodiments, a persistent inflammatory condition cause lameness (e.g., tendonitis or laminitis). In some embodiments, the chronic inflammation that is treated occurs in the liver, gut or respiratory tissues. It is to be understood that any of the conditions stated above may be considered a degenerative condition of large weight-bearing joints.

To "treat" a disease as the term is used herein, means to reduce the frequency or severity of at least one sign or symptom of a disease or disorder experienced by a subject. The compositions described above or elsewhere herein are typically administered to a subject in a therapeutically effective amount, that is, an amount capable of producing a desirable result. The desirable result will depend upon the active agent being administered. For example, a therapeutically effective amount of rAAV particles may be an amount of the particles that are capable of transferring a codon-modified eqIL-1Ra or codon-modified hIL-1Ra encoding gene to an equine or human joint, respectively. A therapeutically effective amount may be an amount that is capable of treating a disease, e.g., OA. As is well known in the veterinary arts, dosage for any one subject depends on many factors, including the subject's size, body surface area, age, the particular composition to be administered, the active ingredient(s) in the composition, time and route of administration, general health, and other drugs being administered concurrently. Treatment may be assessed by a clinical practitioner using standard practices in the art or skills and experience gained in the art (e.g., evaluating inflammation in a joint).

In some embodiments, "administering" or "administration" means providing a material to a subject in a manner that is pharmacologically useful.

In some embodiments, $110^{10}$ to $1 \times 10^{13}$ viral genomes (vgs) (e.g., $5 \times 10^{10}$ to $5 \times 10^{12}$ vg, $1 \times 10^{11}$ to $1 \times 10^{12}$ vg or $2 \times 10^{11}$ to $9 \times 10^{11}$ vg) are administered at a time into a joint to be treated. In some embodiments, the volume of pharmaceutical composition or rAAV being injected is 1-20 ml (e.g., 2-15, 5-12 or 5-10 ml).

In some embodiments, rAAV particles comprising codon-modified eqIL-1Ra encoding gene is administered to an equine joint on a regular basis, for example every 3 months, 6 months or every year or 2-5 years. In some embodiments, rAAV particles comprising codon-modified hIL-1Ra encoding gene is administered to a human joint on a regular basis, for example every 3 months, 6 months or every year or 2-5 years. In some embodiments, rAAV particles comprising codon-modified eqIL-1Ra or hIL-1Ra encoding gene is administered to an equine joint or human joint multiple times (e.g., 2, 3, 4, 5, 6, 7, 8, 9, 10, 13, 14, 15 or 20 times), either at regular intervals of time or irregular intervals of time. In some embodiments, rAAV comprising codon-modified eqIL-1Ra or codon-modified hIL-1Ra encoding gene is administered to a joint only once. In some embodiments, rAAV comprising codon-modified eqIL-1Ra or codon-modified hIL-1Ra encoding gene is administered to an equine or human joint only if symptoms of disease return or increase. In some embodiments, rAAV comprising codon-modified eqIL-1Ra or codon-modified hIL-1Ra encoding gene is administered to an equine or human joint immediately after a condition (e.g., OA) is diagnosed (e.g., within 1 month or 1 year of diagnosis). In some embodiments, rAAV comprising codon-modified eqIL-1Ra or codon-modified hIL-1Ra encoding gene is administered to an equine or human joint before a degenerative condition is diagnosed, but after the occurrence of an event (e.g., an injury) that could lead to a degenerative condition. In some embodiments, rAAV comprising codon-modified eqIL-1Ra or codon-modified hIL-1Ra encoding gene is administered to an equine or human joint immediately after (e.g., within a month) the occurrence of a trauma that could lead to a degenerative condition. In some embodiments, rAAV comprising codon-modified eqIL-1Ra or codon-modified hIL-1Ra encoding gene is administered to an equine or human joint when the first signs of joint disease are observed. Non-limiting examples of symptoms of a degenerative condition of large weight-bearing joint include limping or lameness, joint swelling, decreased turnout activity, and stiffness or decreased movement of the joint.

Since there is a strong correlation between the level of pathology (e.g., total MRI score) at the time of injection of rAAV comprising codon-modified eqIL-1Ra or codon-modified hIL-1Ra encoding gene and downstream IL-1Ra production (see Example 2), treatment can be started after a trauma but before diagnoses of a degenerative disease (e.g., OA). Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

In some embodiments, injection of rAAV comprising codon-modified eqIL-1Ra or codon-modified hIL-1Ra encoding gene into a diseased joint produces a higher level of IL-1Ra production compared to injection of rAAV comprising codon-modified eqIL-1Ra or codon-modified hIL-1Ra encoding gene into an un-diseased or healthy joint. In some embodiments, the production of IL-1Ra in a diseased joint is 1.1-50 times (e.g., 1.1-2, 2-4, 2-10, 5-10, 5-20, 10-20, 20-30, or 30-50 times) higher compared to an un-diseased or healthy joint.

EXAMPLES

Example 1: scAAV-Mediated Gene Delivery of IL-1Ra for the Treatment of Osteoarthritis: Temporal Expression and Biodistribution in an Equine Model The data discussed below show that scAAV can provide sustained expression of eqIL-1Ra in an equine joint, using a codon-modified gene encoding eqIL-1Ra and a Kozak sequence.

Studies targeting the carpal and metacarpophalangeal (mcp) joints of the equine forelimb were undertaken. Since these joints carry 60-65% of the horse's weight during locomotion, are also highly vulnerable to OA secondary to trauma and excessive loading.

To characterize patterns of therapeutic transgene expression and its relative safety following intra-articular delivery, dosing and temporal expression studies were performed using a cDNA for the equine orthologue of IL-1Ra. Using the most effective vector dose, and green fluorescent protein (GFP) as a cytologic reporter gene, the biodistribution of the vector following delivery into healthy joints and those with naturally-occurring OA was examined, with an emphasis on the effect of disease on the local transduced cell populations and systemic dispersion of viral genomes.

Study Animals

Animals used in the study were either donated to the University of Florida or purchased from local farms and training facilities. The endpoints for each parameter of the studies were predefined as described below. No animals were excluded from the data analyses. All animal procedures were conducted in accordance with both the NIH Guide for the Care and Use of Laboratory Animals and the University of Florida Institutional Animal Care and Use Committee. Unless otherwise stated, the horses were housed in groups in large open paddocks, with full freedom of movement.

Construction and Generation of AAV Vectors

To minimize immune recognition of the IL-1Ra transgene product and assemble a pharmacokinetic profile of homologous IL-1Ra gene transfer with the AAV vector, DNA sequences encoding the equine orthologue of IL-1Ra were used as a therapeutic reporter. To maximize expression of the transgenic protein, the native eqIL-1Ra cDNA was codon-modified and a consensus Kozak sequence was inserted immediately upstream of the translation initiation codon (FIG. 1). In this construct, expression of the transgene is driven by the CMV immediate early promoter/enhancer. AAV vectors were packaged in the AAV2.5 capsid at the University of Florida Vector Core or the University of North Carolina Chapel Hill Vector Core by methods previously described.

The cDNAs encoding GFP and modified eqIL-1Ra were directionally inserted into the Sac II and Not I sites of the expression cassette of the pHpa-trs-SK plasmid, a self-complementary (double-stranded DNA) AAV vector variant engineered from the genome of AAV2. In this construct, expression of the transgene is driven by the CMV immediate early promoter/enhancer. AAV vectors were packaged in the AAV2.5 capsid at the University of Florida Vector Core or the University of North Carolina Chapel Hill Vector Core.

In Vivo Dosing and Expression

For in vivo transgene expression analysis, 6 healthy, skeletally mature horses, aged 2-7 years were used. Experiments were performed using both the MCP and intercarpal joints on both forelimbs of each animal. Two weeks prior to injection of vector, synovial fluid from each joint was aspirated by arthrocentesis to establish baseline eqIL-1Ra levels. At the time of injection, in a randomized fashion, fluid volumes of 5 or 10 mL of Lactated Ringer's solution containing 0, $5\times10^{10}$, $5\times10^{11}$ and $5\times10^{12}$ vg of scAAV.eqIL-1Ra were delivered into the 4 forelimb joints of each animal. This strategy was used to provide the greatest assessment of inter-animal variability of transgene expression at the respective doses using a minimum number of subjects. Following injection, the animals were housed under quarantine for 24 hours and monitored closely by veterinary staff. At days 7, 14, and 30 post-injection, and monthly thereafter for a total of 6 months, synovial fluid, peripheral blood and urine were collected from each animal for measurement of eqIL-1Ra content by ELISA. Synovial fluid, peripheral blood and urine will be collected for up to 1 year in a separate experiment to assess longevity of the effect of injecting codon-optimized IL-1Ra into joints.

ELISA for Equine IL-1Ra

Levels of equine IL-1Ra was assayed using specific ELISA (R&D Systems). Synovial fluid samples from both Treated and Control joints were diluted 1:1 with buffered saline containing hyaluronidase at 50 u/ml, and incubated at 37° C. for 30 minutes prior to measuring protein content. Two-fold serial dilutions in reagent diluent (R&D Systems) synovial fluid samples were generated over a wide range to account for assay variability. Each dilution series was generated in duplicate, and each diluted sample was assayed in triplicate wells. Means were calculated from samples with readouts within the boundaries of the standard curves of the respective assays.

Vector Biodistribution In Vivo

To determine systemic biodistribution of the AAV vector following intra-articular injection, the intercarpal joints of 3 healthy horses and 3 with late stage naturally-occurring OA were injected with $5\times10^{12}$ vg of scAAV.GFP diluted in 5 ml Lactated Ringer's solution. The animals were euthanized two weeks later and necropsied. No significant lesions were detected in organs other than the musculoskeletal system. Tissues were harvested from the injected intercarpal joint, the adjacent antebrachiocarpal joint, adjacent quadriceps muscle, ipsilateral MCP joint, contralateral intercarpal joint and adjacent quadriceps muscle, the brain, heart, lung, liver and spleen. The tissues furthest from the injection site were harvested first, and care was taken to minimize cross-contamination of samples. Portions of each sample were placed in DMEM with 10% FBS for subsequent analysis of GFP expression, either by inverted fluorescence microscopy of the fresh tissue, or following paraffin section and immunohistochemical staining. The remaining tissue portions were placed in RNALater (Ambion) and stored at –80° C. for subsequent isolation of genomic DNA (gDNA). To assay for vector genomes, gDNA was extracted from the stored tissue samples using the Qiagen DNeasy Blood and Tissue Kit (Qiagen) according to the manufacturer's instructions. gDNA concentrations were determined using a NanoDrop spectrophotometer (Thermo Scientific). Quantitative real-time PCR was performed using 100 ng gDNA and an Eppendorf RealPlex PCR machine (Eppendorf). Primers were designed to anneal to sequences in the CMV promoter of the vector expression cassette. The sequences for the forward and reverse primers were 5'-CACGCTGTTTGACCTCCATAGAAGACAC (SEQ ID NO: 5) and 5'-TTCTTTGATTTGCACCACCACCG-GATCCG (SEQ ID NO: 6), respectively. For each set of reactions a standard curve was generated using serial dilutions of the pHpa-tr-sk plasmid DNA. PCR reactions specific for equine β-actin (forward primer 5'-CCAGCACGAT-GAAGATCAAG (SEQ ID NO: 7) and reverse primer 5'-GTGGACAATGAGGCCAGAAT (SEQ ID NO: 8)) and without template DNA, were used as positive and negative controls, respectively. All gDNA samples were assayed in triplicate. To test for sample-specific reaction inhibition, aliquots of the gDNA samples were spiked with pHpa-trs-SK vector DNA at 100 copies/μg of gDNA. If 40 copies/μg or more of the spike-in DNA was detected, the gDNA sample was deemed acceptable.

Immunohistochemistry

Tissue samples from the biodistribution study containing visible GFP activity were fixed in paraformaldehyde, processed for histology and paraffin-embedded. Sections cut at 5 μm and mounted on charged slides were deparaffinized, and heat-mediated antigen retrieval was performed. The slides were blocked with 10% normal serum, then incubated for 1 hour at room temperature with rabbit anti-GFP antibody at a 1:200 dilution (Abcam), followed by biotinylated secondary antibody (Invitrogen) for 30 minutes at room temperature at a dilution of 1:500. The slides were mounted with DAPI (Vector Laboratories) and viewed with a fluorescent microscope.

scAAV.eqIL-1Ra Vector Construction and Characterization In Vitro and In Vivo

Figure 2D:
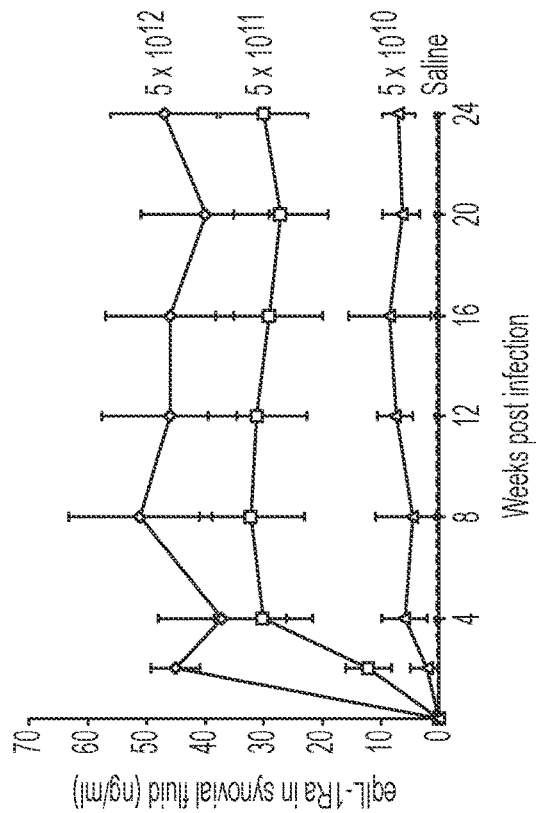
Figure 2A:
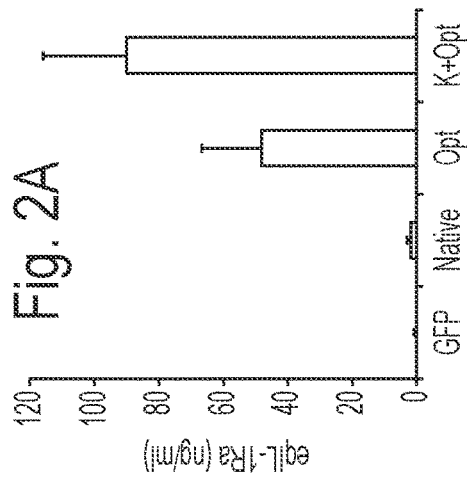

In previous work involving scAAV delivery of the human IL-1Ra cDNA to the equine joint, it was found that, following a peak at 1-2 weeks post-injection, transgene expression steadily diminished, and after 7 weeks, human IL-1Ra was undetectable in synovial fluids by ELISA. This has been attributed to immune recognition of transduced cells expressing the xenogenic transgene product. Although it was possible to generate measurable levels of equine IL-1Ra expression with a recombinant adenoviral vector, protein expression from the native cDNA in general, was relatively modest. Thus, to minimize immune recognition of the IL-1Ra transgene product and maximize expression, the cDNA for the equine IL-1Ra orthologue codon was modified and synthesized both with (SEQ ID NO: 3) and without (SEQ ID NO: 2) a consensus Kozak sequence leader immediately upstream of the translation start site. Following insertion into the scAAV vector plasmid (pHpa-trs-sk), both modified constructs generated a 30-50-fold enhancement of expression over the native sequence in transient transfection assays (FIG. 2A). As the construct including the Kozak sequence consistently provided the greatest levels of eqIL-1Ra expression, it was selected for viral packaging and testing in vivo.

Previous data showed human synovial fibroblasts in culture have a preference for infection with AAV2. Considering possible translation to human testing, the eqIL-1Ra vector construct was packaged in the AAV2.5 capsid, which maintains AAV2 tropism, but shows reduced reactivity with AAV2 neutralizing antibody, prevalent among the human population. Infection of equine synovial fibroblast cultures with a range of doses of the AAV2.5 vector resulted in exceptionally high expression of eqIL-1Ra, which exceeded 10 µg/ml at $10^5$ viral genomes (vg)/cell (FIG. 2B). eqIL-1Ra production did not exceed background in parallel control cultures infected at $10^5$ vg/cell with an AAV2.5 vector containing GFP.

To determine the effect of vector dose on scAAV.eqIL-1Ra expression following intra-articular delivery, an approach designed to provide insight into the intra- and inter-animal variability, using a minimum number of experimental animals was taken. In each of 6 horses, injections of scAAV.eqIL-1Ra at 3 different doses ($5\times10^{10}$, $5\times10^{11}$ and $5\times10^{12}$ vg; FIG. 2D) were distributed in random order among both intercarpal and MCP joints of both forelimbs. The remaining joint was injected with an equivalent volume of delivery vehicle (lactated Ringer's solution) and served as a negative control. Periodically thereafter over a pre-determined interval of ~6 months, synovial fluid was aspirated from each of the forelimb joints, and peripheral blood and urine were collected. eqIL-1Ra content in the biological fluids was measured using commercially available ELISA kits, and interpreted relative to pre-injection values.

Despite receiving AAV in 3 forelimb joints, no adverse effects were observed acutely or at any point during the protocol. Among the control joints, which received only the fluid vehicle, synovial fluid eqIL-1Ra remained at pre-injection levels (<1 ng/ml) throughout (FIG. 2B). In joints receiving virus, dose-related increases in synovial fluid eqIL-1Ra were observed within 2-4 weeks of injection, with mean levels ranging from ~6 ng/ml at $5\times10^{10}$ vg to ~40 ng/ml at $5\times10^{12}$ vg. Peak eqIL-1Ra production occurred at between 4 and 8 weeks post-injection, and was maintained for the remainder of the study (FIG. 2B). In contrast to the near-linear relationship between vector dose and eqIL-1Ra expression seen in culture, the 100-fold increase in vector dose over the range tested in vivo, only resulted in a ~10-fold increase in IL-1Ra expression. Moreover the increase dose from $5\times10^{11}$ to $5\times10^{12}$ vg only elevated synovial fluid eqIL-1Ra 1.5-fold. Thus it is possible that these values are at or near the maximum.

AAV2. 5 Transgene Expression in Healthy and OA Joints

As the $5\times10^{12}$ vg dose of scAAV.eqIL-1Ra consistently provided the highest eqIL-1Ra production intra-articulalry and appeared reasonably safe, it was selected for further characterization in vivo. To determine the influence of the OA environment on the local and systemic distribution of the AAV vector and transduced cell populations, an scAAV vector construct containing the coding sequence for GFP was packaged in the AAV2.5 capsid. Then, $5\times10^{12}$ vg of scAAV.GFP was injected into one intercarpal joint of 3 healthy horses and 3 horses with advanced, naturally-occurring OA (FIGS. 3A-3B). Two weeks later, the horses were euthanized, and tissues were collected from the injected joints and sites throughout the body.

Figure 4A:
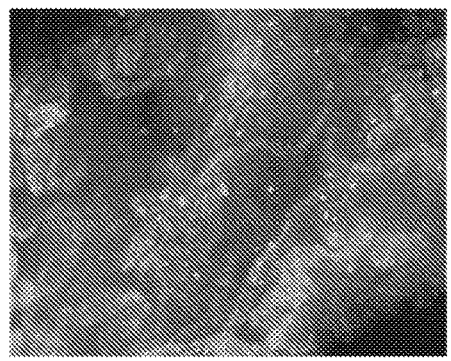
FIGS. 4A-4H show GFP expression in equine OA tissues following intra-articular gene delivery with scAAV. Additional fields of interest from results described in FIG. 2. The intercarpal joints of 3 horses with naturally-occurring late-stage OA were injected with $5\times10^{12}$ vg of scAAV.GFP, and two weeks later the joint tissues were collected and analyzed for fluorescence. Shown is GFP expression in tissues with pathologic changes characteristic of established OA.
Figure 4E:
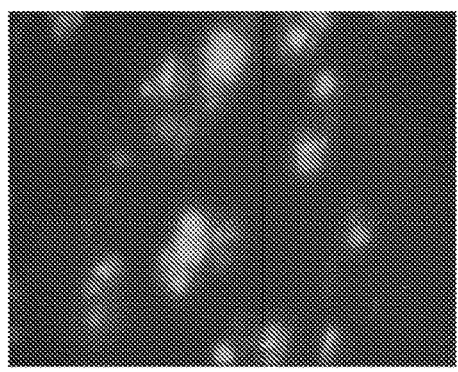
Figure 4B:
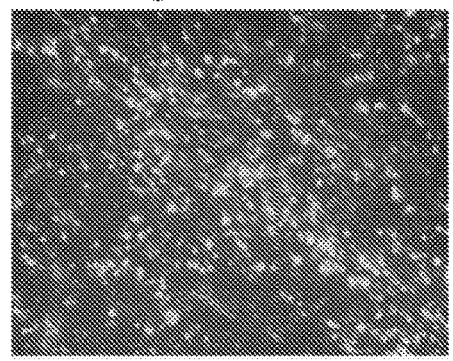
Figure 4F:
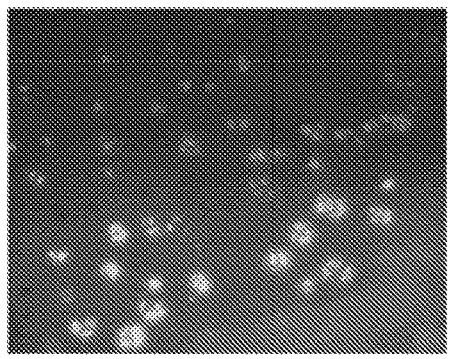

Similar to AAV serotypes tested previously, in each of the healthy joints the predominant site of GFP expression was the synovium. Examination of the fresh tissue samples revealed abundant fluorescent cells throughout the lining of the joint capsule, which were often concentrated in thicker villous regions (FIGS. 3C-3D). GFP activity was visible in articular cartilage shavings, but was faint and limited to scattered isolated cells (FIGS. 3G-3H). In striking contrast, GFP activity in OA synovium was much higher than the healthy joints. These samples often were brilliantly fluorescent, even at low magnification (FIG. 3E). The density of the fluorescent cells was visibly higher across the entire expanse of the synovial lining, but particularly so in regions with inflammation and synovitis (FIGS. 3F and 4A-4B). Similar to healthy joints, the fluorescent cells were almost exclusively delimited to the synovium and subsynovium, and only rarely seen in the supporting fibrous tissues.

Figure 4C:
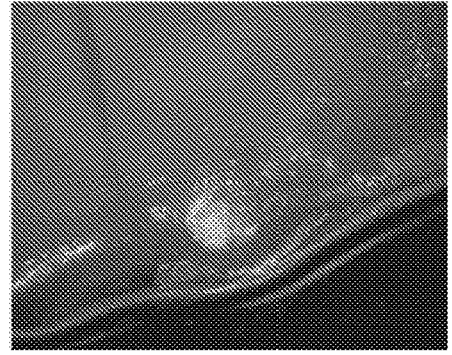
Figure 4G:
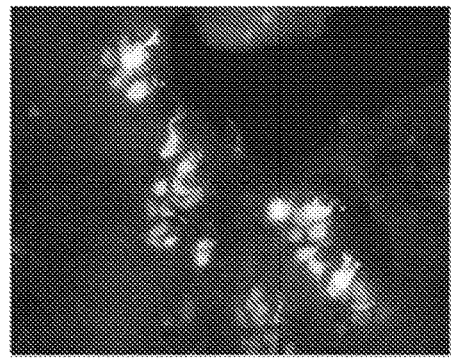
Figure 4D:
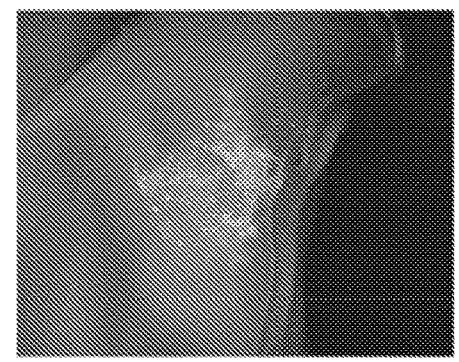
Figure 4H:
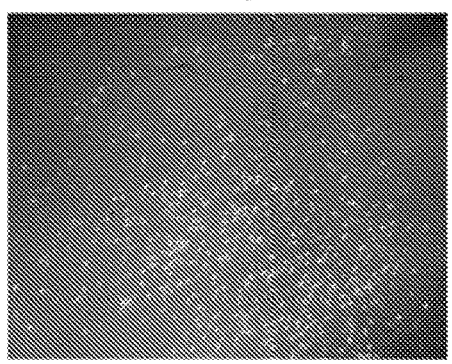

The OA cartilage showed the most dramatic enhancement in GFP activity, as populations of brightly fluorescent cells were readily apparent in all shavings recovered (FIGS. 3J-3K). Shavings harvested near full thickness erosions, often contained focal regions with intense fluorescence (FIGS. 3L and 4C-4D), and frequently contained cells with spindle-shaped morphology, consistent with dedifferentiation to fibrochondrocytes (20). Higher magnification showed that GFP expression was visible in a majority of the resident chondrocyte population, but was particularly prominent in chondrocyte clusters characteristic of OA cartilage (FIGS. 3M and 4E-4G). Pockets of brightly fluorescent cells were also visible along the surfaces of osteophytes recovered from the margins of the OA joints (FIGS. 3N and 4H).

Figure 2C:
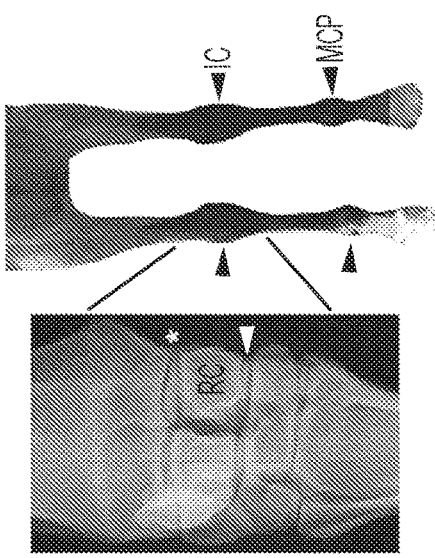

For both healthy and OA joints receiving virus, the synovium of the antebrachiocarpal joint of the carpus was the only tissue outside the intercarpal joint that contained visible fluorescence. Despite its location immediately proximal to the site of injection (FIG. 2C), only sparse fluorescent cells were seen, and in only a few of the harvested samples (FIG. 3O).

In a related observation, it was found that the GFP expression in shavings of healthy cartilage (barely detectable at harvest), increased dramatically after 48 hours incubation in explant culture, such that dense populations of vividly fluorescent cells appeared throughout the matrix in each sample (FIG. 3I). This suggested that a large percentage of the chondrocytes had actually been transduced by the virus in situ, but failed to express the fluorescent reporter protein above the visible threshold in the context of the healthy joint.

AAV2. 5 Biodistribution

To assess the emigration of the AAV vector from the joint following intra-articular injection, total DNA was isolated from the tissue samples and assayed for vector genome content by quantitative PCR. As shown in Table 1, the systemic distribution of vector genomes was largely consistent with visible GFP activity. For all animals, the tissues from the joints receiving virus showed the highest vector genome content. Though there was wide variation among individuals, on average, the vector DNA in the synovium was ~30-50 fold higher than in cartilage, with no significant differences between the OA and normal joints. Detectable, but considerably fewer vector genomes were found in the synovium of the adjacent antebrachiocarpal joint in horses from both groups. Outside the carpus, one animal from the healthy group showed a low number of vector genomes in the liver; while the liver and spleen from one animal in the OA group were also positive for vector content. Altogether, under both healthy and diseased conditions >99.7% of the AAV vector genomes detected were in the joint tissues. These results indicate that the vector is primarily contained within the joint, and while the OA environment may enhance transgene expression intra-articularly, it does not appear to meaningfully impact extra-articular vector dispersion.

TABLE 1

Distribution of AAV.GFP genomes following injection in the intercarpal joint of healthy horses and those with naturally-occurring OA. Values represent vector genome copies per microgram of genomic DNA and are means of at least three replicates ± SEM. Tissues and locations are in reference to the injected joint.

| | Healthy | | | OA | | |
|---|---|---|---|---|---|---|
| Tissue | Horse 1 | Horse 2 | Horse 3 | Horse 4 | Horse 5 | Horse 6 |
| Synovium intercarpal joint | 178,313 ± 559 | 66,022 ± 167 | 16,460 ± 114 | 212,262 ± 237 | 15,590 ± 280 | 142,033 ± 720 |
| Cartilage intercarpal joint | 3,349 ± 43 | 989 ± 109 | 1,726 ± 59 | 2,499 ± 69 | 887 ± 19 | 6,177 ± 55 |
| Antebrachiocarpal synovium | 159 ± 86 | 202 ± 9 | ND | ND | ND | 84 ± 16 |
| Peri-articular muscle | ND | ND | ND | ND | ND | ND |
| Contralateral intercarpal synovium | ND | ND | ND | ND | ND | ND |
| Contralateral quadriceps | ND | ND | ND | ND | ND | ND |
| Ipsilateral MCP | ND | ND | ND | ND | ND | ND |
| Brain | ND | ND | ND | ND | ND | ND |
| Heart | ND | ND | ND | ND | ND | ND |
| Liver | ND | ND | 45 ± 5 | 380 ± 15 | ND | ND |
| Lung | ND | ND | ND | ND | ND | ND |
| Spleen | ND | ND | ND | 277 ± 64 | ND | ND |

ND, not detected

The studies described in this Example show that in a large mammalian joint, the genetically modified cells can sustain elevated levels of protein synthesis for over 6 months. Articular pathologies, such as acute trauma or chronic erosive disease, can increase viral transduction and transgenic expression significantly. Moreover, in both healthy and diseased joints, the vast majority of the vector DNA is retained in the articular tissues, and local overproduction of IL-1Ra is not detected in the circulation. Based on the data, it may be predicted that the genetically modified cells can sustain elevated levels of protein synthesis for longer than 6 months (e.g., up to 1 year, up to 2 years, up to 5 years or up to 10 years).

Advantages to the Equine Model

Local AAV-mediated gene transfer was explored previously in human joints for the treatment of rheumatoid arthritis (26), and entered Phase II study (27). Unfortunately, measurement of the transgenic protein (a tumor necrosis factor α antagonist) produced in the joints was not part of the protocol, and no information emerged from this trial regarding the level and duration of transgenic expression achieved in human joints. However, given its relationship to therapeutic efficacy, this information will be critical to effective clinical application.

Toward this end, the use of the equine system has proven particularly informative, allowing the capacity of an AAV vector for gene delivery to be tested on a scale relevant to human treatment, and in the context of naturally occurring OA. The ability to serially aspirate synovial fluid enables direct quantitation of intra-articular transgene expression and the generation of meaningful pharmacokinetic profiles. Additionally, the use of outbred animals, their variable responses to osteochondral injury, inherent differences in behavior and healing capacity, provide a reasonable simulation of the variability associated with the treatment of humans in a clinical setting.

Gene Expression Patterns

Substantially higher expression of the GFP reporter was observed in association with the cellular and morphologic changes in the joint typical of advanced OA. In the synovium, chronic inflammatory stimulation frequently induces hyperplasia, angiogenesis, leukocytic infiltration, and fibrotic thickening. While AAV-mediated GFP expression appeared consistently higher throughout the synovium of OA joints, fluorescence was especially pronounced in regions of synovitis, where the increased cellularity served to heighten the density of target cells receptive to AAV transduction.

The most notable increase in GFP expression in the OA joints occurred in the articular cartilage. In stark contrast with cartilage from healthy joints, where GFP+ cells were sparse and fluorescence was barely visible, abundant brightly fluorescent cells appeared throughout the shavings harvested from the OA joints, with the most striking increases at sites with obvious signs of erosion. While the loss of matrix integrity likely facilitated entry and diffusion of the vector particles in OA cartilage, the present data suggests that much of the heightened transgene expression in cartilage (and synovium) arises from inflammatory and stress-induced activation of the cytomegalovirus (CMV) immediate early promoter.

Chondrocytes in healthy cartilage largely exist in a non-distressed, resting state. In OA, degradation of the cartilage matrix diminishes its protective properties, causing excessive mechanical loading on the local chondrocytes. These abnormal forces stimulate signaling from nuclear factor κB (NF-κB) and stress-induced mitogen activated protein kinases (MAPK), which drives the metabolism of the normally quiescent chondrocytes into a highly activated state. The activated chondrocytes undergo a marked change in phenotype; they become proliferative, secrete high levels of inflammatory cytokines, and release proteolytic enzymes that further degrade the local matrix. Although the CMV immediate early promoter is generally considered a high-level constitutive promoter, transcription from this element is known to be responsive to NF-κB, and signal transduction from p38 and other stress-activated protein kinases. In the native virus, engagement of these pathways is required for activation of CMV immediate early promoter and initiation of viral replication. Similarly, inflammation and cellular stress can significantly increase the expression of transgenes under its control (40, 43-45). In this respect, OA cartilage is enriched with stress-activated chondrocytes, which populate regions of erosion at high density. GFP expression was also prominent at sites of chondrocyte proliferation and cluster formation, and along the surfaces of osteophytes, which arise from persistent activation of chondro-osseous progenitors at the transition from cartilage to synovium. Potent activation of GFP expression was also seen in the cartilage shavings from healthy joints following incubation in explant culture. As no additional vector was added to the shavings, this induction had to arise from vector DNA already present in the chondrocytes. Therefore, it must reflect a dramatic increase in metabolic and transcriptional activity in transduced chondrocytes from the stress of harvest and/or change in growth conditions.

Thus, while a number of reports describe the generation of synthetic inflammation-inducible promoter systems for gene therapy applications, the CMV immediate early promoter, at least within the context of OA and the large mammalian joint, appears to be innately disease regulated. Moreover, the regional differences in GFP expression seen in OA cartilage indicate the potential with an AAV vector and an expression cassette driven by the CMV promoter to preferentially direct transgene expression to the areas of articular cartilage under the greatest pathologic stress. This lays the foundation for development of targeted chondroprotective and regenerative strategies.

Altogether, the data from this study demonstrate scAAV can provide sustained expression of a homologous therapeutic transgene in a large mammalian joint. Furthermore, gene delivery appears to be significantly more efficient in the context of OA, enabling enhanced expression in synovial tissues and in articular cartilage.

Example 2: scAAV-Mediated Gene Delivery of IL-1Ra for the Treatment of Osteoarthritis: Pharmacokinetics and Efficacy in an Equine Model In this Example, eqIL-1Ra delivery using rAAV in an equine osteochondral fragmentation (OCF) model of OA is discussed. Data demonstrate that a gene based therapy using recombinant AAV can provide effective delivery of anti-arthritic proteins in joints of human proportion. Distinct from any existing treatment for OA, this approach has the capacity to block painful symptoms and erosive progression of disease.

Study Animals

Animals used in the study were either donated to the University of Florida or purchased from local farms and training facilities. For the efficacy study in the OCF model, the animal handlers and evaluators were blinded to treatment group assignment. One horse originally assigned to the Treated group was euthanized midway through the experimental protocol due to pneumonia arising from complications during anesthesia recovery. This animal was subsequently replaced to fulfill the subject number needed for statistical analyses. The endpoints for each parameter of the studies were predefined as described below. All data presented are from the 10 Treated, and 10 Control animals that completed the experimental protocol; no animals were excluded from the data analyses. Discussion of outlying data points is clearly delineated in the text and figures. All animal procedures were conducted in accordance with both the NIH Guide for the Care and Use of Laboratory Animals and the University of Florida Institutional Animal Care and Use Committee. Unless otherwise stated, the horses were housed in groups in large open paddocks, with full freedom of movement.

Construction and Generation of AAV Vectors

To minimize immune recognition of the IL-1Ra transgene product and assemble a pharmacokinetic profile of homologous IL-1Ra gene transfer with the AAV vector, DNA sequences encoding the equine orthologue of IL-1Ra were used as a therapeutic reporter. To maximize expression of the transgenic protein, the native eqIL-1Ra cDNA (57, 58) was codon-modified (16)(GeneArt) and a consensus Kozak sequence (17) was inserted immediately upstream of the translation initiation codon (FIG. 1). In this construct, expression of the transgene is driven by the CMV immediate early promoter/enhancer (30). AAV vectors were packaged in the AAV2.5 capsid (18, 19), at the University of Florida Vector Core or the University of North Carolina Chapel Hill Vector Core by methods previously described (7).

ELISA for equine IL-1β, IL-1Ra and $PGE_2$

Levels of equine IL-1Ra (R&D Systems), $PGE_2$ (R&D Systems) and equine IL-1β (GenWay) were assayed using specific ELISA. Synovial fluid samples from both Treated and Control joints were diluted 1:1 with buffered saline containing hyaluronidase at 50 u/ml, and incubated at 37° C. for 30 minutes prior to measuring protein content. Two-fold serial dilutions in reagent diluent (R&D Systems) of blood serum and synovial fluid samples were generated over a wide range to account for assay variability. Each dilution series was generated in duplicate, and each diluted sample was assayed in triplicate wells. Means were calculated from samples with readouts within the boundaries of the standard curves of the respective assays.

Efficacy Study in an OCF Model

Twenty thoroughbred horses between 2 and 9 years of age, and of mixed gender were used in this phase of the study. The animals were healthy and free of lameness or radiographic signs of carpal joint disease. Prior to induction of the disease model, the horses were conditioned by treadmill exercise 5 days/week for 3 weeks. For each exercise day, the horses were trotted (4-5 m/sec) for 2 min, galloped (~9 m/sec) for 2 min, and again trotted for 2 min. Prior to further use, the animals were randomly divided into equal Treated and Control groups.

Following treadmill conditioning, under general anesthesia an arthroscopic examination was performed bilaterally in both intercarpal joints. During the procedure, in one randomly assigned joint, an 8 mm osteochondral lesion was created medially off the radiocarpal bone, using an osteotome aligned perpendicular to the articular surface (14). The fragment was allowed to remain attached to the capsular tissues. To mimic a natural injury (59), debridement of the parent bone (14) was not performed. The contralateral joint in each horse served as a sham operated internal control. All horses were housed in a stall for 7 days post-operatively and received appropriate veterinary care.

Two weeks post-surgery, following surgical scrub of the forelimb joints, the OCF joint of the horses assigned to the Treated group received an injection of $5 \times 10^{12}$ vg of scAAV.eqIL-1Ra suspended in Lactated Ringer's solution in a total volume of 5 mL. Horses in the Control group received 5 mL of Lactated Ringer's solution without virus. One week after injection, the horses were returned to the 5 day/week treadmill exercise program above, for 10 weeks. During training, the horses were given weekly clinical examinations and lameness assessments. At the conclusion of the 10 week training period, a final arthroscopic examination was performed on both intercarpal joints. The fragment was removed, and the lesion in the parent bone was debrided and repaired. Following recovery, the animals were returned to the research herd. Digital images were collected during both arthroscopic procedures. Radiographic and MR imaging were performed immediately prior to both arthroscopic procedures and prior to treatment at week 0. On alternate weeks throughout the protocol, peripheral blood and urine were collected, and synovial fluid was aspirated from both intercarpal joints.

Lameness Evaluation

Forelimb lameness was evaluated weekly during the 10 week, post-operative treadmill training period by both subjective and objective methods. Subjective visual lameness assessments were performed by two qualified evaluators, appropriately blinded, with the horses on the treadmill at a walk and a trot (~4 m/sec) according to guidelines of the American Association of Equine Practitioners. The grading system was as follows: 0, lameness not perceptible; 1, lameness is difficult to observe and is not consistently apparent; 2, lameness is difficult to observe at a walk or when trotting in a straight line but consistently apparent under certain circumstances; 3, lameness is consistently observable at a trot under all circumstances; 4, lameness is obvious at a walk; 5, lameness produces minimal weight bearing in motion and/or at rest or a complete inability to move.

For objective gait assessment, an inertial sensor-based motion analysis system (Lameness Locator®; Equinosis) was used, that was designed specifically to detect and evaluate lameness in horses (22, 23). For each weekly session, at least 3 measurements were taken at a ~4 m/sec trot on a treadmill. Each measurement was calculated from a minimum of 30 uninterrupted strides. Lameness was calculated as a vector sum using the mean maximum head difference (HDmax) and mean minimum head difference (HDmin) between the left and right strides for every stride in each measurement (22, 23). HDmax is the difference in the maximum head height that occurs after right forelimb stance to that which occurs after left forelimb stance. HDmin is the difference in minimum head height that occurs during right forelimb stance to that which occurs during left forelimb stance. For each session the means of the HDmax and HDmin from at least 3 measurements were used to calculate the vector sum (VS) as follows:

$$VS = \sqrt{HDmax^2 + HDmin^2} \quad (22, 23)$$

For both subjective and objective assessments, lameness values at week 1 were used as baselines for each horse. Subsequent measurements for each horse calculated as percent change relative to baseline.

MR Imaging and Evaluation

MR examinations of both carpi were performed using a Toshiba Titan (Japan) 1.5 Tesla high-field unit. Under general anesthesia, the horses were placed in left lateral recumbency with each carpus in partial flexion (15-25 degrees) in a quadrature transmit/receive knee coil (QD Knee). The MR coil and sequences were selected and modified to be clinically applicable in live horses (24), and included sagittal and axial proton density (PD), dorsal T2-weighted, axial T2 short-tau inversion recovery (STIR), sagittal proton density with fat suppression (PD-FS), and sagittal spoiled gradient echo with fat suppression (SPGR-FS). Total acquisition time was approximately one hour and twenty minutes for all sequences on both limbs. The MR scans for each horse were examined by three evaluators blinded to treatment group assignment. Following review of the scans from the 6 MR sequences for each intercarpal joint and time point, scores were assigned for the predominant pathologies associated with the model, including synovial effusion, synovial proliferation, severity of the osteochondral lesion, damage to articular cartilage, marrow edema in the radiocarpal bone, sclerosis of the radial carpal and third carpal bones, joint capsule edema and capsular fibrosis, using a scale from 0 to 10, where 0 represented normal and 10 represented severe pathology (60, 61). Scoring was based on involvement within the intercarpal joint only. Final scores for each pathology represent means of the 3 evaluators. Total MR pathology scores were determined from the sum of the individual pathologies (60, 61).

Arthroscopic Evaluation

Both intercarpal joints of the horses in the Treated and Control groups were examined and imaged arthroscopically, following generation of the osteochondral lesion and again at the endpoint of the experimental protocol. Digital images collected during the procedures were scored by three blinded evaluators for the size of the lesion and degree of fragment repair, integration of border zone of the defect with surrounding cartilage, appearance of surface cartilage overall, and appearance of synovium and ligaments. Based on criteria from Dymock et al. (62) a scoring system from 0 to 10 was used where 0 represented normal, and 10 represented severe pathology.

Histology

The osteochondral fragment and synovial tissue removed during the endpoint arthroscopy were fixed in paraformaldehyde, decalcified and paraffin-embedded. Serial sections of 5 μm were mounted on charged slides, deparaffinized and rehydrated, and blocked in 3% peroxide/methanol for 10 minutes at room temperature. Alternate sections in regions of interest were stained with hematoxylin and eosin (H&E) and toluidine blue, respectively. The section series were analyzed and graded by two blinded evaluators using a grading system adapted from McIlwraith et al. (63). Briefly, articular cartilage integrity was scored based on signs of chondrocyte necrosis, cluster formation, fibrillation, and/or focal cell loss. The synovial membrane was evaluated and graded based on signs of vascularity, intimal hyperplasia, subintimal edema and/or subintimal fibrosis. Leukocytic infiltration was scored on the same scale as a readout of inflammation. Finally, the subchondral bone and repair interface was evaluated for matrix quality, osteochondral lesions, bone remodeling, and osteochondral splitting. The total score was calculated from the sum of the individual scores.

Measurement of Capsid-Targeted Neutralizing Antibody

Methods were adapted from those described by Li et al. (64). Synovial fluid was digested with hyaluronidase as described for ELISA, and blood serum was incubated at 56° C. for 30 minutes for complement inactivation. Using serumless media a series of two-fold serial dilutions were generated from the pre-treated serum or synovial fluid. The diluted samples were mixed with ~1×10 9 vg scAAV.eqIL-1Ra packaged in AAV2.5 capsid in a total volume of 250 μl, and incubated for 1 hour at 37° C. to allow antibody binding. The mixtures were then added to confluent cultures of equine synovial fibroblasts in 24-well plates containing 250 μl culture medium (500 μl/well total volume). After incubation for 48 hours under standard culture conditions, the conditioned media were harvested and assayed for eqIL-1Ra content by ELISA. NAb titers were indicated as the inverse of highest dilution capable of reducing by 50% the eqIL-1Ra levels produced by cells infected with AAV.eqIL-1Ra pre-incubated as above, but without biological fluids.

Statistical Analysis

Analyses consisted of independent sample t tests, analysis of covariance t tests with baseline scores serving as covariates, and correlational analyses. In most cases one-tailed tests were employed since, a priori, it was hypothesized that the horses receiving treatment with scAAV.eqIL-1Ra would have lower mean values from the diagnostic assessments employed, thus dictating the direction of the tail. The experimental layout was a two-sample repeated measures design with horses randomly assigned to the treatment groups (Treated or Control). The data was analyzed using multiple independent sample t tests. With a Type I error of 0.05, 80% power and an effect size d=1.3 (large), a total of 20 horses in the study were required to show a treatment effect at any time. As it was anticipated that correlations would exist between baseline measurements and the repeated measurements, the power for the study exceeded 80% with the inclusion of baseline measurements as covariates.

Efficacy of scAAV.eqIL-1Ra in an Osteochondral Fragment Model of OA

To assess the functional capacity of AAV-mediated IL-1Ra expression, an OCF model of OA, adapted from Frisbie et al. (14), was used. For this study (diagrammed in FIG. 5A), 20 healthy thoroughbred horses were randomly assigned into equal groups: Treated and Control. In one intercarpal joint of each animal, an 8 mm osteochondral lesion was generated arthroscopically in the medial aspect of the radiocarpal bone. The contralateral joint received a parallel arthroscopic examination and served as a sham-operated internal control. At two weeks post-surgery (study day 0) the OCF joint of the horses in the Treated group received an injection of $5 \times 10^{12}$ vg of scAAV.eqIL-1Ra. The horses in the Control group received a similar injection volume of saline. One week later (allowing time for onset of transgenic IL-1Ra expression), the horses were placed on an athletic training schedule for 10 weeks, which in the context of the osteochondral injury induces pathologies consistent with early stage OA.

At the conclusion of the athletic training, the intercarpal joints of the animals were evaluated arthroscopically, and the osteochondral fragment and adjacent synovium were collected for analysis. The lesion was debrided and repaired, and following recovery, the animals were returned to the research herd.

Local and Systemic eqIL-1Ra Levels Following Intra-Articular Injection of Vector ELISA measurement of synovial fluids from the OCF joints of the Treated group showed a significant increase in eqIL-1Ra content, throughout the 12 week study. Reaching a mean level of 214 ng/ml at two weeks post-injection, eqIL-1Ra production was ~4-fold greater than measured in healthy joints receiving the same viral dose (FIG. 5B). Over the course of the training protocol, eqIL-1Ra expression gradually dropped, and at week 12 measured ~59 ng/ml, close to that observed in normal joints. In synovial fluids from OCF joints of the Control group, as well as sham-operated joints of both groups, IL-1Ra remained at pre-treatment levels throughout, and did not exceed 1 ng/ml. While the plot of the mean eqIL-1Ra levels in the Treated joints showed a reasonably smooth trend, expression among the individual animals was highly variable (FIG. 5C), especially at the earliest time point, where expression ranged more than 230-fold, and in one animal exceeded 930 ng/ml. By the end of the study, much of the early variation had resolved, and the range narrowed to ~30-fold, with the highest expression at 119 ng/ml.

To assay for leakage of transgenic protein from the joint, eqIL-1Ra content in urine and peripheral blood serum at each time point was also measured. eqIL-1Ra in urine remained consistently low (<3 ng/ml) with no meaningful differences between Treated and Control groups (FIG. 5D). Similarly, mean eqIL-1Ra in the blood serum remained less than 4 ng/ml for 9 of the 10 horses in both groups (FIG. 5E). Prior to injection, one horse from each of the Treated and the Control groups showed blood serum eqIL-1Ra levels that exceeded 100 ng/ml without obvious cause (FIG. 5F). Despite circulating eqIL-1Ra in these animals subsequently rising to >500 ng/ml, no accompanying increase in eqIL-1Ra was seen in the synovial fluid of the OCF joint of the Control horse, or the sham-operated joints of either horse, and eqIL-1Ra in each consistently remained below 1 ng/ml. Endogenous IL-1 in synovial fluids remained below the level of detection (16 pg/ml) in all biological fluids throughout the course of the study. These results indicate that under these treatment conditions, transgenic eqIL-1Ra expression is functionally contained within the joint and does not elevate IL-1Ra levels systemically. Conversely, increases in eqIL-1Ra in blood serum by up to 200-fold over normal have no detectable effect on eqIL-1Ra content in synovial fluids.

Consistent with the findings of others (21), an increase in mean levels of AAV2.5 neutralizing antibody (NAb) with time was observed in both blood serum and synovial fluid of the horses receiving vector (FIG. 5G). NAb titer in synovial fluids of the joints receiving vector was consistently higher than blood. No NAb was detected in fluids of Control animals at any time.

Reduced lameness associated with scAAV.eqIL-1Ra treatment

Figure 6A:
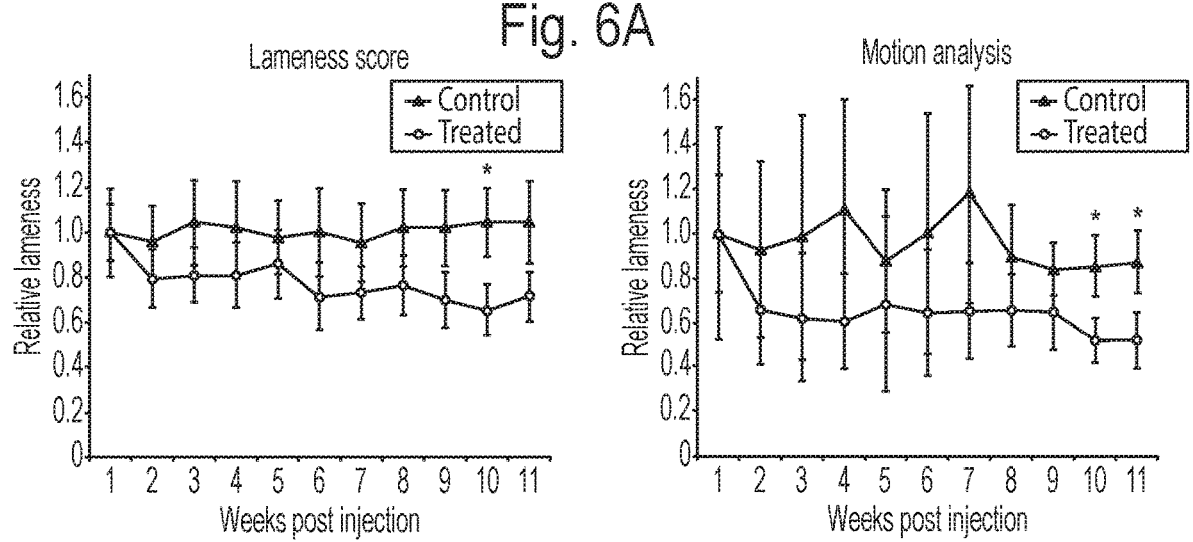
FIGS. 6A-6B show changes in joint lameness and synovial fluid $PGE_2$ levels following treatment with scAAV.eqIL-1Ra.
Figure 6B:
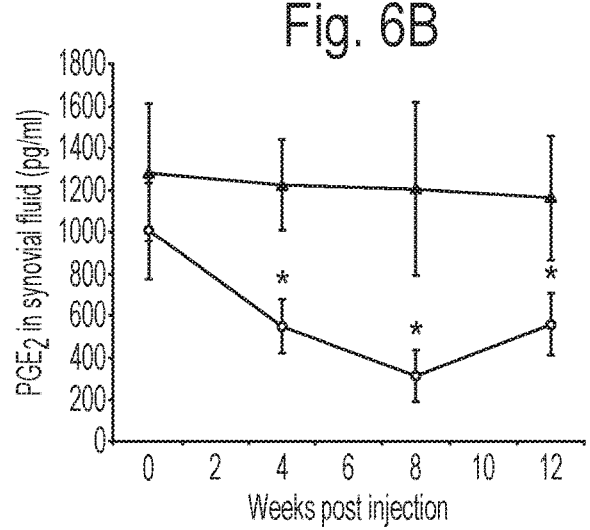

To assess treatment effect on joint pain, forelimb lameness was evaluated using visual lameness scoring and by motion analysis using wireless detection of attached inertial sensors (22, 23). Lameness was plotted over time as the mean percent change relative to the start of training at week 1 post-injection. Relative to Control, animals in the Treated group showed a gradual but progressive reduction in lameness by both methods, which peaked at 36% (P=0.03) improvement at week 10 by visual assessment (FIG. 6A, left panel) and 40% (P=0.04) at weeks 10 and 11 by motion analysis (FIG. 6A, right panel). In agreement with reduced joint pain by these functional indices, measurement of prostaglandin E2 ($PGE_2$) content in joint fluids showed >50% reduction in the Treated group over Control from week 4 through the conclusion of the protocol (FIG. 6B).

scAAV.eqIL-1Ra Delivery Improves Repair of an Acute Osteochondral Injury

Figure 7A:
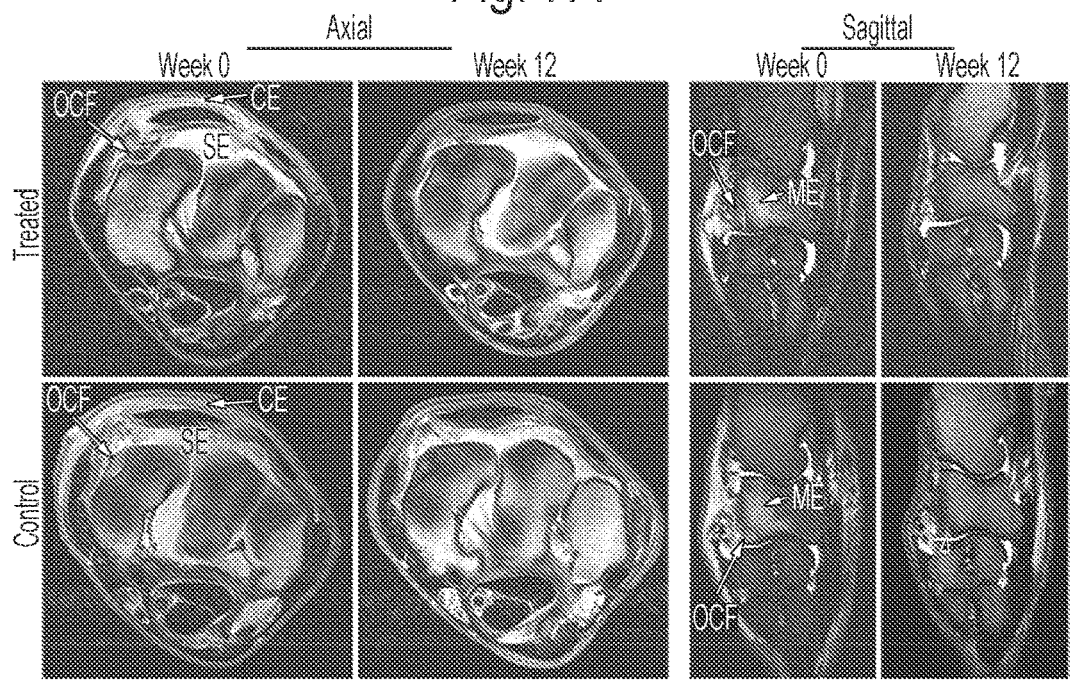
FIGS. 7A-7B show an evaluation of MR images for changes in tissue pathology in OCF joints treated with scAAV.eqIL-1Ra. Both intercarpal joints of all horses were scanned by MR imaging immediately prior to treatment (Week 0) and at the end of the experimental protocol (Week 12). The scans were scored for synovial effusion, synovial proliferation, the severity of the osteochondral lesion (OCF size), marrow edema in the radiocarpal bone, sclerosis of the radial carpal and third carpal bones, and joint capsule edema and fibrosis on a scale from 0 to 10, where 0=normal and 10=severe pathology.
Figure 7B:
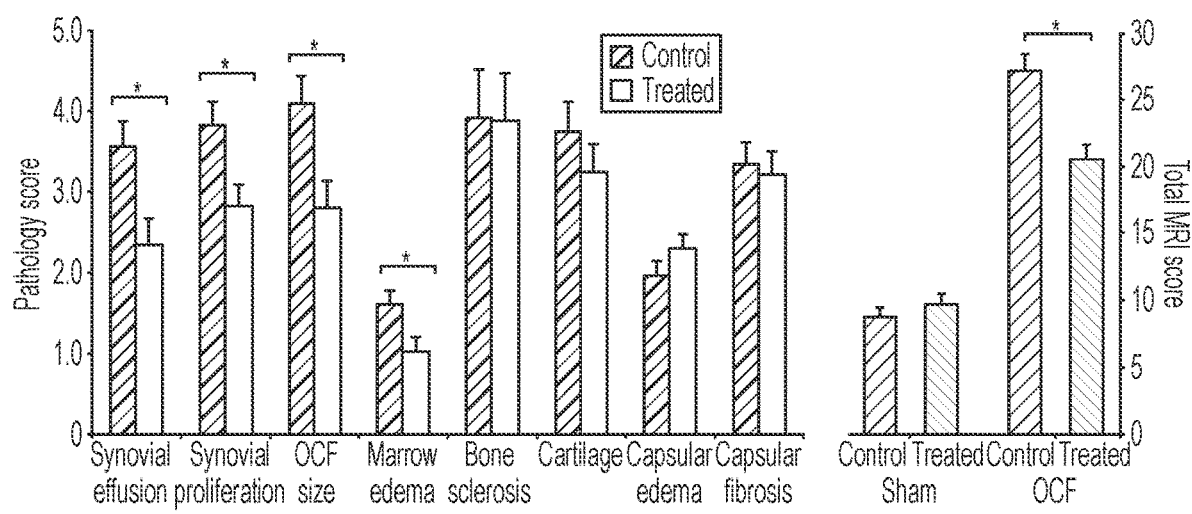

Radiographic abnormalities were seen in all OCF joints at two weeks post-surgery and at endpoint; however, the anatomic complexity of the carpal joint coupled with position variability between imaging sessions prevented uniform temporal comparisons among horses. Magnetic resonance (MR) images acquired at the same time points provided a clearer representation of the changes in joint pathology associated with each osteochondral injury, allowing comparison of pre-treatment and end-point scores over the 12 week interval for each individual (24). In all cases, the changes in the MR images were primarily found medially, in the vicinity of the surgically generated fracture (FIG. 7A). At two weeks post injury, well-defined high intensity signal delineated the boundaries of each fragment in the radial carpal bone, and was accompanied variably among OCF joints by increased density of the adjacent bone, regional fluid accumulation in the marrow (marrow edema), joint effusion, synovial hyperplasia, as well as fibrotic expansion and edema of the joint capsule. Using the pretreatment scores (week 0) for these pathologies as baselines for each horse, an analysis of covariance with the MR scans acquired at endpoint was performed to assess the effects of treatment on joint morphology. As reflected in FIGS. 7A-7B, both groups showed equivalent changes in the joint capsule, with similar loss of capsular edema and increased fibrotic thickening, which was attributed primarily to the arthroscopic procedure and fluid infusion and less to the osteochondral lesion. Consistent with the anti-inflammatory properties of IL-1Ra intra-articularly, the OCF joints in the Treated group showed significantly reduced joint effusion (34%, P=0.008) and synovial proliferation (27%, P=0.008) relative to the Control group (FIG. 7B). The Treated group also showed a 32% (P=0.01) improvement in fracture repair and a 36% (P=0.02) reduction in marrow edema. Across the major pathologies induced by the OCF, the Treated joints showed a 25% (P=0.001) reduction in total pathologic score relative to the Control group (FIG. 7B).

Arthroscopic images taken during generation of the OCF and at endpoint (immediately prior to surgical repair of the fragment), were also blindly scored for pathologies. Covariate analyses were performed using the pre-treatment scores (week −2) as baselines (FIGS. 8A-8B). As shown in FIG. 8A, these results were largely consistent with those from the MR images. Animals in the Treated group showed significantly improved repair of the osteochondral lesion (29%, P=0.03) and the articular cartilage adjacent to the fracture (17%, P=0.02). Although there were trends toward improvement in the global cartilage scores and ligament inflammation, these did not achieve statistical significance individually. Cumulatively, however, across all pathologic parameters the Treated OCF joints showed 24% (P=0.04) improvement in total arthroscopic pathology scores (FIG. 8A). In agreement with these data, in 8/10 horses in the Treated group the osteochondral lesions had repaired to the extent that they required a chisel for removal of the fragment originally created. Conversely, in 7/10 horses in the Control group, the repair tissue was spongy and soft during indentation test, and the fragment was readily removed with arthroscopic forceps.

Histologic examination of the recovered fragments and adjacent synovial tissues showed significant differences in the quality of the repair bone at the boundary of OCF lesion (FIGS. 8B-8C). Consistent with the findings from arthroscopy and MRI, in the Treated group the bony tissue at the interface appeared more mature, with greater mineralization and formation of lamellar bone with defined osteons (FIG. 8D). The repair tissue in the Control group was mainly comprised of primary woven bone. Although there was a strong trend toward improved cartilage, the scores fell just outside the range for statistical significance (P 5=0.06). Modest reductions in mean scores for synovial infiltration and fibrosis were also observed, but these also were not statistically significant. By the criteria evaluated, the Treated joints showed 24% (P=0.003) improvement in total pathologic score relative to the untreated Control group (FIG. 8C).

Association Between eqIL-1Ra Levels and Joint Pathology

Figure 9A:
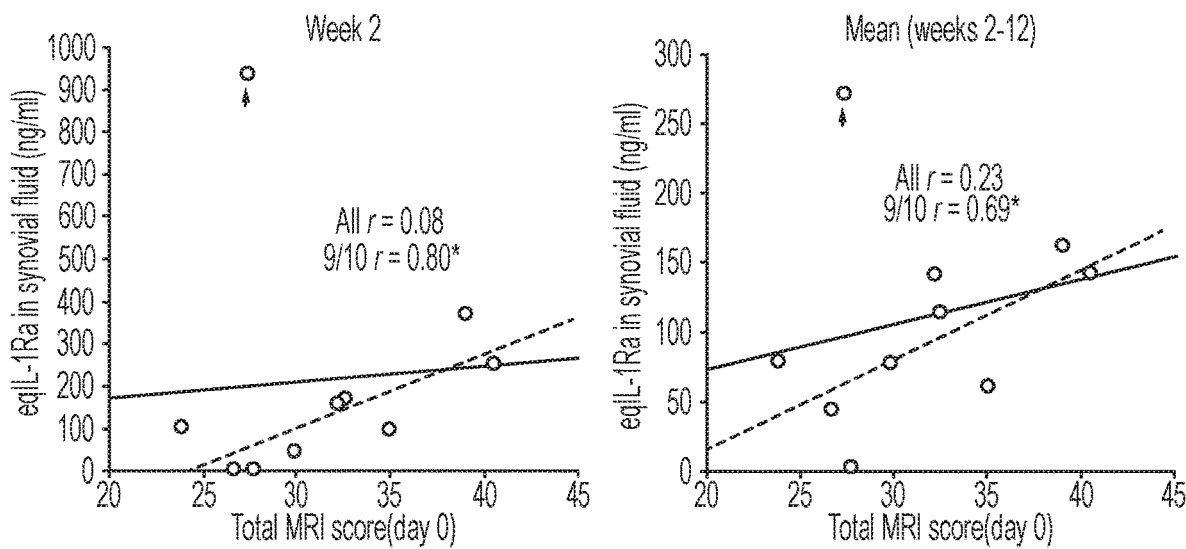
FIGS. 9A-9B show associations between eqIL-1Ra expression and joint pathology.

Having seen increased GFP activity in equine joints with naturally-occurring OA (see, Example 1), an association between eqIL-1Ra expression in the OCF joints of the Treated group and the severity of joint pathology at the time of injection was correlated. Comparing for each animal the total MRI scores at week 0, with peak synovial fluid eqIL-1Ra levels at week 2 post-injection (FIG. 9A, left panel), and mean eqIL-1Ra levels across the 10 week study (FIG. 9A, right panel), no significant correlation was noted using all 10 horses. If however, the horse with eqIL-1Ra expression of 930 ng/ml at week 2 is considered an outlier, a strong direct correlation is found between joint pathology at injection and eqIL-1Ra produced at week 2 (r=0.80, P=0.01) and mean eqIL-1Ra levels across all time points (r=0.69, P=0.03). Thus, for 90% of the animals there was a significant direct association between joint pathology at the time of treatment, and the amount of transgenic IL-1Ra produced in the joint.

Figure 9B:
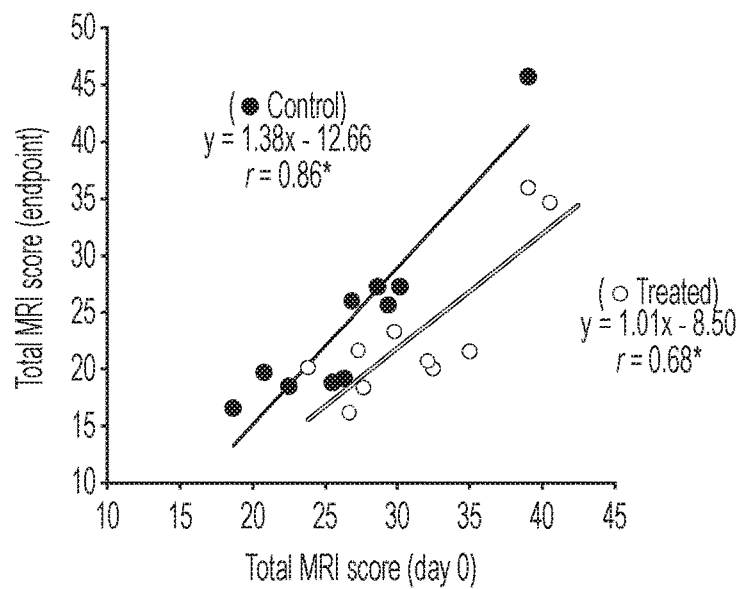

Interestingly, in Treated OCF joints, mean synovial fluid IL-1Ra levels over the 10-week course of the study ranged from ~6 to 159 ng/ml, yet no significant correlation was seen with therapeutic benefit. A plot of the total MRI scores of each horse immediately before injection versus those at endpoint illustrates the effect of treatment with AAV.eqIL-1Ra relative to saline (FIG. 9B). Using the formulas for the best-fit lines for the Treated and Control groups, a consistent 24-25% improvement with scAAV.eqIL-1Ra is estimated regardless of the starting pathology. Considering that the animals with the worst overall pathology, in general, produced the highest levels of eqIL-1Ra (FIG. 9A) a fairly consistent treatment effect was observed in all Treated animals regardless of the specific amount of IL-1Ra produced. Given the variability in transgene expression among the animals (FIGS. 5A-5G and 9A), these data suggest that for each animal the level of IL-1Ra produced in each of the joints receiving scAAV.eqIL-1Ra achieved the maximum level of efficacy in this model system.

These studies show that in a large mammalian joint, direct intra-articular AAV-mediated gene delivery can elevate steady-state levels of a secreted, homologous, therapeutic gene product (IL-1Ra) in synovial fluids more than 50-fold over the endogenous background. Despite variable expression among Treated joints in the context of an acute osteochondral lesion, sustained increase in IL-1Ra provided meaningful benefit, such that a single AAV.IL-1Ra administration at two weeks post-injury reduced joint pain and intra-articular inflammation and improved the endogenous repair of damaged bone and adjacent cartilage.

Altogether these data demonstrate that AAV can provide persistent, therapeutically relevant IL-1Ra expression in joints proportional in size to the human knee, and when applied soon after joint injury can protect against symptomatic development of an acute model of pre-OA. Furthermore, no adverse response to vector or transgene was observed, and at least within the equine system intra-articular overexpression of IL-1Ra provided no apparent risk of systemic immunosuppression.

Similar to a report by Ishihara et al. (21), an increase in NAb titer following vector delivery was observed, both in synovial fluid and the blood serum. However, considering the apparent efficiency of transduction of articular chondrocytes, which are likely to be a relatively stable cell population, frequent vector re-administration may not be necessary. Moreover, as the primary antibody titer recedes, circulating NAb at low titer may be incapable of inhibiting a supraphysiological bolus of AAV virions delivered intra-articularly.

Gene Expression Patterns

Conventional methods of drug delivery provide the practitioner a reasonable degree of control, in that a defined dose can be administered to achieve a largely predictable effect. In the current paradigm, cells in the articular tissues are genetically modified by a recombinant virus to continuously synthesize and secrete an anti-arthritic protein, IL-1Ra, into the joint space and local tissues. However, as the amount of transgenic IL-1Ra produced at any particular time reflects the collective synthesis of the modified cells present in the joint, levels can vary widely (both within and among individuals) based on the nature of the cell populations originally modified by the virus and ensuing changes in their composition and metabolic activity.

In this respect, the present data in the equine joint show that the pathologic status of the joint at the time of treatment has a potent, direct influence on transgenic expression. AAV.IL-1Ra delivery into inflamed joints with an acute osteochondral injury resulted in a ~5-fold increase in mean IL-1Ra levels over that seen in healthy joints. Although IL-1Ra in synovial fluid ranged more than 100-fold among the OCF joints at two weeks post treatment, in 9 out of 10 animals there was a strong direct correlation between the level of pathology (total MRI score) at the time of injection and downstream IL-1Ra production. Coincident with the loss of inflammation and the healing of the fracture, the heightened IL-1Ra expression likewise gradually diminished, and at the 12 week endpoint approached levels produced in normal joints.

IL-1Ra as a Therapeutic Gene in OA

In joints treated with scAAV.eqIL-1Ra, a mean improvement in pathology of ~25%, relative to the Control group was observed. Consistent with its role as an anti-inflammatory (49), sustained over-expression of eqIL-1Ra improved mobility, and reduced joint effusion and synovitis. Although there was evidence of protection in the cartilage adjacent to the lesion, the effect was not joint-wide. In this acute injury model, cartilage degeneration distal to the osteochondral lesion was modest, making any changes due to treatment difficult to detect. With respect to the capacity of this treatment to inhibit cartilage erosion more fully, it is expected that the efficacy and safety of local scAAV.eqIL-1Ra delivery in a chronic OA model over a 12 month time frame would show that sustained IL-1Ra expression leads to a more distinct chondroprotective effect.

Interestingly, despite a reduction in synovial fluid $PGE_2$, the Treated group showed significantly improved repair of the osteochondral fracture relative to Control. This finding appears to conflict with the literature indicating vital roles for cyclooxygenase-2 and the prostaglandins in fracture repair (50, 51). These molecules, though, primarily contribute to the acute inflammatory phase of bone healing, which begins to resolve around 7-14 days post-injury, giving way to repair processes of cellular differentiation and matrix synthesis (52). While acute inflammation is required to initiate the repair process, persistent inflammation can impede activation of the Wnt/β-catenin pathway and osteoblast differentiation, which inhibits bone repair (53, 54). Therefore by administering the vector at two-weeks post-surgery, the reduced inflammatory signaling from IL-1Ra overexpression likely served to enhance osteoblast differentiation during the repair phase leading to improved healing. Along these lines, treatment with AAV.IL-1Ra in a similar time frame post joint injury may provide therapeutic/prophylactic benefits in post-traumatic OA, combining reduced inflammation and enhanced tissue repair with potential downstream chondroprotection.

Despite intra-articular IL-1Ra expression over a wide range, no correlation between synovial fluid eqIL-1Ra content and therapeutic benefit was observed. This was attributed to the mode of action of IL-1Ra as a competitive inhibitor of the IL-1 type 1 receptor (4). Due to the potency of IL-1 signaling, IL-1Ra must be present in 100 to 1000 fold excess over IL-1 to completely inhibit its activity (55, 56). In the OCF joints, synovial fluid IL-1 was below the limit of detection (16 pg/ml). Thus, in the majority of treated joints, IL-1Ra was present in a 6,000-fold excess, and least 400-fold in the joints with the lowest expression. As IL-1Ra has no known agonist effect (4), once available IL-1 receptors are occupied, additional IL-1Ra can provide no further benefit. Considering these points, then consistent ~24-25% improvement in joint pathology observed in the Treated group likely reflects the maximum benefit achievable in this disease model with this method of IL-1Ra delivery.

Overall these data indicate that IL-1Ra is well-suited to intra-articular gene therapies for OA. It does not require sophisticated regulation, only synthesis levels above the therapeutic threshold. Once achieved, overproduction has little apparent adverse consequence, and thus, it is tolerant of the wide variation associated with viral-mediated gene delivery in vivo. The data indicate that IL-1Ra gene delivery is unlikely to be a cure for OA, as it is only capable of blocking the IL-1 signaling component of an extremely complex disease involving large-scale pathologies and processes mediated at the level of the tissues and organism. Nonetheless, as IL-1 is a primary driver of the inflammatory cascade and plays an active role in the majority of erosive processes in OA, which are mediated at the cellular level, it has the potential to provide meaningful benefit to patients over a broad spectrum of disease severity.

Altogether, the data from this study demonstrate that a gene based therapy using recombinant AAV can provide safe, persistent, effective delivery of an anti-arthritic protein to joints of human proportion. Moreover AAV.IL-1Ra applied soon after joint injury can reduce symptomatic development in an acute model of pre-OA. Distinct from any existing treatment, this approach has the capacity to block painful symptoms and erosive progression of disease. Based on the findings here, AAV.IL-1Ra combines efficacy with an appropriate level of safety, providing a profile supportive of clinical testing in human and equine OA.

Example 3: Generation of Codon-Modified Human IL-1Ra cDNA

A cDNA for human interleukin-1 receptor antagonist (IL-1Ra) that provided the highest expression (secretion) of IL-1Ra from genetically modified cells was generated with the goal of clinical application in a gene therapy protocol. Toward this goal, the native cDNA sequence codon was modified using the human optimization algorithms of two DNA synthesis companies—GeneScript and GeneArt. Two modified IL-1Ra sequences were ordered from GeneArt, with and without a consensus Kozack sequence immediately upstream of the translation start site. Upon receipt of the synthetic cDNAs, all three were directionally inserted into the Sac II and Not I sites of the expression cassette of the pHpa-trs-SK plasmid, a self-complementary (double-stranded DNA) AAV vector variant engineered from the genome of AAV2, and transformed into Sure II bacterial cells. In this construct, expression of the transgene is driven by the CMV immediate early promoter/enhancer. Following verification of the respective inserts, large scale cultures were generated of the 3 new constructs, as well as two pre-existing scAAV vector constructs containing a) the native cDNA for human IL-1Ra, and b) the coding sequence for green fluorescent protein (GFP). The plasmids from each culture were isolated and twice purified over cesium chloride gradients. The concentrations of each DNA preparation were determined by spectrophotometer and visualization in agarose gels.

To determine the relative expression of IL-1Ra protein from each construct, equivalent amounts of each plasmid were transfected into HEK 293 cells at ~70% confluency. Approximately 48 hours later, the conditioned medium from each culture was collected, and the human IL-1Ra content was measured by ELISA using commercially available kits. FIG. 10 shows the mean levels from three transfections with each plasmid construct. As expected, no measurable IL-1Ra was seen in the cultures receiving the scAAV.GFP plasmid. IL-1Ra expression from the 3 codon-modified cDNAs exceeded that from the native sequence by ~2-4 fold. While IL-1Ra expression from both constructs synthesized by GeneArt exceeded that from GeneScript, the GeneArt cDNA with the consensus Kozak sequence provided the highest IL-1Ra expression.

Figure 11:
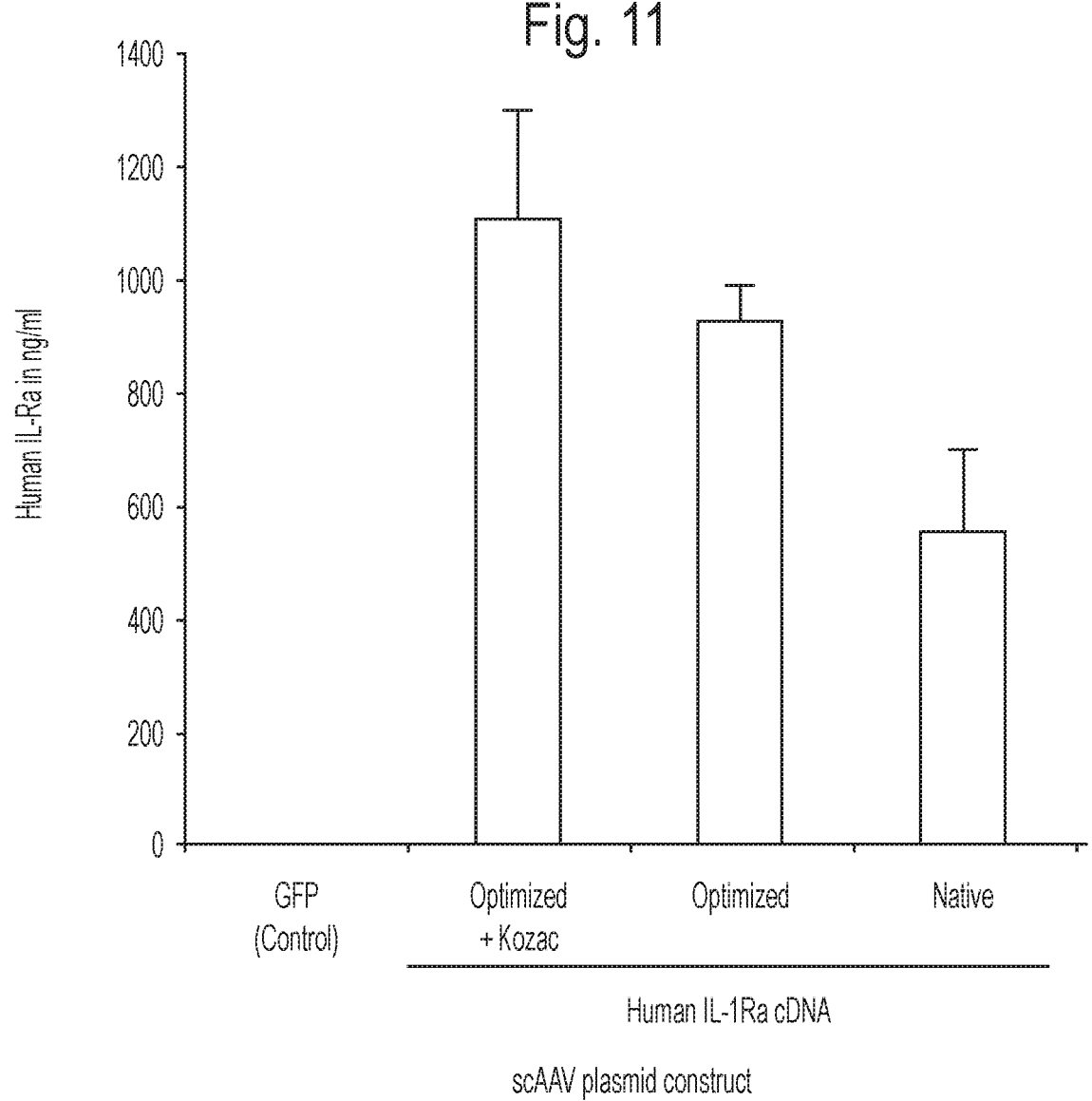
FIG. 11 shows secretion of human IL-1Ra in human osteosarcoma cells transfected with scAAV vector plasmids containing native and modified human IL-1Ra cDNA. Error bars show the SEM.

To confirm the results observed in 293 cells (FIG. 10) in a different cell line, equal amounts of the scAAV vector plasmids containing the GeneArt codon modified human IL-1Ra cDNAs (with and without the Kozak leader sequence), were transfected into cultures of human osteosarcoma (OS) cells at ~75% confluency. Parallel cultures of OS cells were transfected with scAAV vector plasmids containing the coding sequences for GFP or native human IL-1Ra. Approximately 48 hours later, the media from the cultures was harvested and the IL-1Ra content was measured by commercially available ELISA. FIG. 11 shows the mean levels from three transfections with each plasmid. Similar to that seen in the 293 cells (FIG. 10), human IL-1Ra expression from the OS cells receiving the modified constructs was substantially higher than that from the native human sequence, with the modified sequence with a Kozak sequence producing the highest levels overall.

Figure 12:
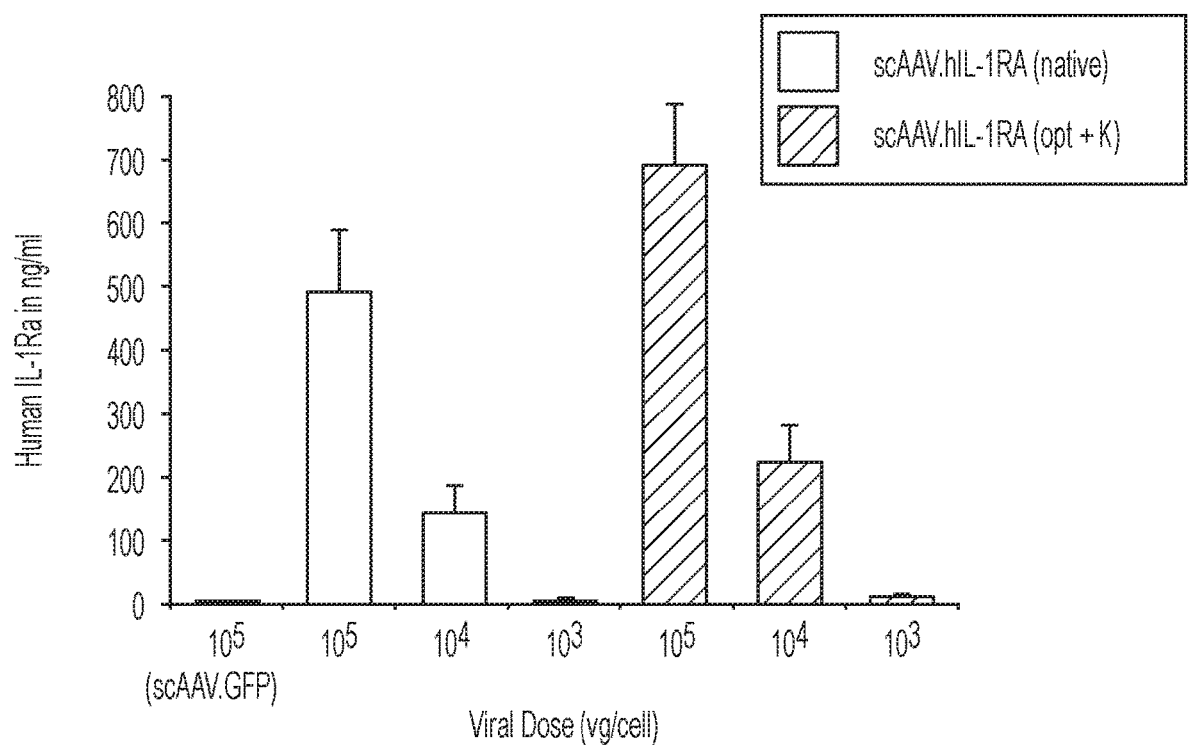
FIG. 12 shows secretion of human IL-1Ra in primary human synovial fibroblasts infected with AAV2 capsids containing native and codon-modified human IL-1Ra cDNA. n=3 infections; error bars represent +SEM.

To test the expression level of the modified human IL-1Ra cDNA in the context of viral-mediated gene delivery, the scAAV vector plasmids containing the coding sequences for a) GFP, b) the native human IL-1Ra, and c) the GeneArt codon-modified human IL-1Ra sequence with Kozak leader (opt+K) were packaged into the AAV2 capsid. The titers of the respective viral preparations were determined by both PCR and slot blot assays. Cultures of primary human synovial fibroblasts were infected with both IL-1Ra viral preparations over a range of doses from $10^3$ to $10^5$ DNAse resistant viral genomes (vg) per cell. Parallel infection with $10^5$ vg/cell of scAAV.GFP was used as a negative control. At day 5 post-infection the media conditioned by the infected cultures was harvested and analyzed for IL-1Ra content by ELISA. As shown in FIG. 12, the cells infected with the codon-modified human IL-1Ra vector produced higher levels of transgenic human IL-1Ra at all viral doses.

FIG. 13 shows the alignment of the native human IL-1Ra cDNA and the codon modified IL-1Ra sequence including the underlined Kozak sequence. The alignment shows that 105 of the 534 nucleotides in the native IL-1Ra cDNA sequence were changed in the modification. While the DNA sequence has been altered to improve translation and expression of the IL-1Ra RNA, the amino acid sequence of the translated protein is identical to the native protein.

REFERENCES

1. R. F. Loeser, S. R. Goldring, C. R. Scanzello, M. B. Goldring, Osteoarthritis: a disease of the joint as an organ. *Arthritis Rheum* 64, 1697-1707 (2012).
2. S. A. Olson, P. Horne, B. Furman, J. Huebner, M. Al-Rashid, V. B. Kraus, F. Guilak, The role of cytokines in posttraumatic arthritis. *J Am Acad Orthop Surg* 22, 29-37 (2014).
3. M. Kapoor, J. Martel-Pelletier, D. Lajeunesse, J. P. Pelletier, H. Fahmi, Role of proinflammatory cytokines in the pathophysiology of osteoarthritis. *Nat Rev Rheumatol* 7, 33-42 (2011).
4. W. P. Arend, M. Malyak, C. J. Guthridge, C. Gabay, Interleukin-1 receptor antagonist: role in biology. *Annu Rev Immunol* 16, 27-55 (1998).
5. X. Chevalier, P. Goupille, A. D. Beaulieu, F. X. Burch, W. G. Bensen, T. Conrozier, D. Loeuille, A. J. Kivitz, D. Silver, B. E. Appleton, Intraarticular injection of anakinra in osteoarthritis of the knee: a multicenter, randomized, double-blind, placebo-controlled study. *Arthritis Rheum* 61, 344-352 (2009).
6. J. D. Kay, E. Gouze, T. J. Oligino, J. N. Gouze, R. S. Watson, P. P. Levings, M. L. Bush, A. Dacanay, D. M. Nickerson, P. D. Robbins, C. H. Evans, S. C. Ghivizzani, Intra-articular gene delivery and expression of inter-leukin-1Ra mediated by self-complementary adeno-associated virus. *J Gene Med* 11, 605-614 (2009).
7. R. S. Watson, T. A. Broome, P. P. Levings, B. L. Rice, J. D. Kay, A. D. Smith, E. Gouze, J. N. Gouze, E. A. Dacanay, W. W. Hauswirth, D. M. Nickerson, M. J. Dark, P. T. Colahan, S. C. Ghivizzani, scAAV-mediated gene transfer of interleukin-1-receptor antagonist to synovium and articular cartilage in large mammalian joints. *Gene Ther* 20, 670-677 (2013).
8. C. H. Evans, S. C. Ghivizzani, P. D. Robbins, Arthritis gene therapy and its tortuous path into the clinic. *Transl Res* 161, 205-216 (2013).
9. H. Madry, M. Cucchiarini, Advances and challenges in gene-based approaches for osteoarthritis. *J Gene Med* 15, 343-355 (2013).
10. K. R. Vincent, B. P. Conrad, B. J. Fregly, H. K. Vincent, The pathophysiology of osteoarthritis: a mechanical perspective on the knee joint. *PMR* 4, S3-9 (2012).
11. L. R. Goodrich, A. J. Nixon, Medical treatment of osteoarthritis in the horse—a review. *Vet J* 171, 51-69 (2006).
12. D. M. McCarty, P. E. Monahan, R. J. Samulski, Self-complementary recombinant adeno-associated virus (scAAV) vectors promote efficient transduction independently of DNA synthesis. *Gene Ther* 8, 1248-1254 (2001).
13. D. M. McCarty, H. Fu, P. E. Monahan, C. E. Toulson, P. Naik, R. J. Samulski, Adeno-associated virus terminal repeat (TR) mutant generates self-complementary vectors to overcome the rate-limiting step to transduction in vivo. *Gene Ther* 10, 2112-2118 (2003).
14. D. D. Frisbie, S. C. Ghivizzani, P. D. Robbins, C. H. Evans, C. W. McIlwraith, Treatment of experimental equine osteoarthritis by in vivo delivery of the equine interleukin-1 receptor antagonist gene. *Gene Ther* 9, 12-20 (2002).
15. E. Gouze, J. N. Gouze, G. D. Palmer, C. Pilapil, C. H. Evans, S. C. Ghivizzani, Transgene persistence and cell turnover in the diarthrodial joint: implications for gene therapy of chronic joint diseases. *Mol Ther* 15, 1114-1120 (2007).
16. S. Fath, A. P. Bauer, M. Liss, A. Spriestersbach, B. Maertens, P. Hahn, C. Ludwig, F. Schafer, M. Graf, R. Wagner, Multiparameter RNA and codon optimization: a standardized tool to assess and enhance autologous mammalian gene expression. *PLoS One* 6, e17596 (2011).
17. M. Kozak, Interpreting cDNA sequences: some insights from studies on translation. *Mamm Genome* 7, 563-574 (1996).
18. C. Li, N. Diprimio, D. E. Bowles, M. L. Hirsch, P. E. Monahan, A. Asokan, J. Rabinowitz, M. Agbandje-McKenna, R. J. Samulski, Single Amino Acid Modification of Adeno-Associated Virus Capsid Changes Transduction and Humoral Immune Profiles. *J Virol*, (2012).

19. D. E. Bowles, S. W. McPhee, C. Li, S. J. Gray, J. J. Samulski, A. S. Camp, J. Li, B. Wang, P. E. Monahan, J. E. Rabinowitz, J. C. Grieger, L. Govindasamy, M. Agbandje-McKenna, X. Xiao, R. J. Samulski, Phase 1 gene therapy for Duchenne muscular dystrophy using a translational optimized AAV vector. *Mol Ther* 20, 443-455 (2012).
20. L. J. Sandell, T. Aigner, Articular cartilage and changes in arthritis. An introduction: cell biology of osteoarthritis. *Arthritis Res* 3, 107-113 (2001).
21. A. Ishihara, J. S. Bartlett, A. L. Bertone, Inflammation and immune response of intra-articular serotype 2 adeno-associated virus or adenovirus vectors in a large animal model. *Arthritis* 2012, 735472 (2012).
22. K. G. Keegan, C. G. MacAllister, D. A. Wilson, C. A. Gedon, J. Kramer, Y. Yonezawa, H. Maki, P. F. Pai, Comparison of an inertial sensor system with a stationary force plate for evaluation of horses with bilateral forelimb lameness. *Am J Vet Res* 73, 368-374 (2012).
23. K. G. Keegan, D. A. Wilson, J. Kramer, S. K. Reed, Y. Yonezawa, H. Maki, P. F. Pai, M. A. Lopes, Comparison of a body-mounted inertial sensor system-based method with subjective evaluation for detection of lameness in horses. *Am J Vet Res* 74, 17-24 (2013).
24. M. D. Winter, The basics of musculoskeletal magnetic resonance imaging: terminology, imaging sequences, image planes, and descriptions of basic pathologic change. *Vet Clin North Am Equine Pract* 28, 599-616 (2012).
25. L. R. Goodrich, J. N. Phillips, C. W. McIlwraith, S. B. Foti, J. C. Grieger, S. J. Gray, R. J. Samulski, Optimization of scAAVIL-1ra In Vitro and In Vivo to Deliver High Levels of Therapeutic Protein for Treatment of Osteoarthritis. *Mol Ther Nucleic Acids* 2, e70 (2013).
26. P. J. Mease, K. Hobbs, A. Chalmers, H. El-Gabalawy, A. Bookman, E. Keystone, D. E. Furst, P. Anklesaria, A. E. Heald, Local delivery of a recombinant adenoassociated vector containing a tumour necrosis factor alpha antagonist gene in inflammatory arthritis: a phase 1 dose-escalation safety and tolerability study. *Ann Rheum Dis* 68, 1247-1254 (2009).
27. P. J. Mease, N. Wei, E. J. Fudman, A. J. Kivitz, J. Schechtman, R. G. Trapp, K. F. Hobbs, M. Greenwald, A. Hou, S. A. Bookbinder, G. E. Graham, C. W. Wiesenhutter, L. Willis, E. M. Ruderman, J. Z. Forstot, M. J. Maricic, K. H. Dao, C. H. Pritchard, D. N. Fiske, F. X. Burch, H. M. Prupas, P. Anklesaria, A. E. Heald, Safety, tolerability, and clinical outcomes after intraarticular injection of a recombinant adeno-associated vector containing a tumor necrosis factor antagonist gene: results of a phase 1/2 Study. *J Rheumatol* 37, 692-703 (2010).
28. C. R. Scanzello, S. R. Goldring, The role of synovitis in osteoarthritis pathogenesis. *Bone* 51, 249-257 (2012).
29. R. Rollin, F. Marco, J. A. Jover, J. A. Garcia-Asenjo, L. Rodriguez, L. Lopez-Duran, B. Fernandez-Gutierrez, Early lymphocyte activation in the synovial microenvironment in patients with osteoarthritis: comparison with rheumatoid arthritis patients and healthy controls. *Rheumatol Int* 28, 757-764 (2008).
30. E. V. Schmidt, G. Christoph, R. Zeller, P. Leder, The cytomegalovirus enhancer: a pan-active control element in transgenic mice. *Mol Cell Biol* 10, 4406-4411 (1990).
31. P. Lane Smith, M. C. Trindade, T. Ikenoue, M. Mohtai, P. Das, D. R. Carter, S. B. Goodman, D. J. Schurman, Effects of shear stress on articular chondrocyte metabolism. *Biorheology* 37, 95-107 (2000).
32. F. Berenbaum, Signaling transduction: target in osteoarthritis. *Curr Opin Rheumatol* 16, 616-622 (2004).
33. C. J. Malemud, Protein kinases in chondrocyte signaling and osteoarthritis. *Clin Orthop Relat Res*, S145-151 (2004).
34. S. Rigoglou, A. G. Papavassiliou, The NF-κB signalling pathway in osteoarthritis. *Int J Biochem Cell Biol* 45, 2580-2584 (2013).
35. M. B. Goldring, K. B. Marcu, Cartilage homeostasis in health and rheumatic diseases. *Arthritis Res Ther* 11, 224 (2009).
36. M. B. Goldring, Chondrogenesis, chondrocyte differentiation, and articular cartilage metabolism in health and osteoarthritis. *Ther Adv Musculoskelet Dis* 4, 269-285 (2012).
37. R. Liu-Bryan, R. Terkeltaub, Emerging regulators of the inflammatory process in osteoarthritis. *Nat Rev Rheumatol* 11, 35-44 (2015).
38. P. Loser, G. S. Jennings, M. Strauss, V. Sandig, Reactivation of the previously silenced cytomegalovirus major immediate-early promoter in the mouse liver: involvement of NFkappaB. *J Virol* 72, 180-190 (1998).
39. R. A. Johnson, S. M. Huong, E. S. Huang, Activation of the mitogen-activated protein kinase p38 by human cytomegalovirus infection through two distinct pathways: a novel mechanism for activation of p38. *J Virol* 74, 1158-1167 (2000).
40. R. U. Svensson, J. M. Barnes, O. W. Rokhlin, M. B. Cohen, M. D. Henry, Chemotherapeutic agents up-regulate the cytomegalovirus promoter: implications for bioluminescence imaging of tumor response to therapy. *Cancer Res* 67, 10445-10454 (2007).
41. J. L. Meier, M. J. Keller, J. J. McCoy, Requirement of multiple cis-acting elements in the human cytomegalovirus major immediate-early distal enhancer for viral gene expression and replication. *J Virol* 76, 313-326 (2002).
42. X. F. Liu, X. Wang, S. Yan, Z. Zhang, M. Abecassis, M. Hummel, Epigenetic control of cytomegalovirus latency and reactivation. *Viruses* 5, 1325-1345 (2013).
43. W. Bruening, B. Giasson, W. Mushynski, H. D. Durham, Activation of stress-activated MAP protein kinases up-regulates expression of transgenes driven by the cytomegalovirus immediate/early promoter. *Nucleic Acids Res* 26, 486-489 (1998).
44. M. Ramanathan, G. Haskó, S. J. Leibovich, Analysis of signal transduction pathways in macrophages using expression vectors with CMV promoters: a cautionary tale. *Inflammation* 29, 94-102 (2005).
45. A. J. Simpson, G. A. Cunningham, D. J. Porteous, C. Haslett, J. M. Sallenave, Regulation of adenovirus-mediated elafin transgene expression by bacterial lipopolysaccharide. *Hum Gene Ther* 12, 1395-1406 (2001).
46. A. V. Miagkov, A. W. Varley, R. S. Munford, S. S. Makarov, Endogenous regulation of a therapeutic transgene restores homeostasis in arthritic joints. *J Clin Invest* 109, 1223-1229 (2002).
47. M. Khoury, J. Adriaansen, M. J. Vervoordeldonk, D. Gould, Y. Chernajovsky, P. Bigey, C. Bloquel, D. Scherman, P. P. Tak, C. Jorgensen, F. Apparailly, Inflammation-inducible anti-TNF gene expression mediated by intra-articular injection of serotype 5 adeno-associated virus reduces arthritis. *J Gene Med* 9, 596-604 (2007).
48. F. A. van de Loo, A. S. de Hooge, R. L. Smeets, A. C. Bakker, M. B. Bennink, 0. J. Arntz, L. A. Joosten, H. M. van Beuningen, P. K. van der Kraan, A. W. Varley, W. B. van den Berg, An inflammation-inducible adenoviral expression system for local treatment of the arthritic joint. *Gene Ther* 11, 581-590 (2004).
49. K. A. Elsaid, L. Zhang, Z. Shaman, C. Patel, T. A. Schmidt, G. D. Jay, The impact of early intra-articular administration of interleukin-1 receptor antagonist on lubricin metabolism and cartilage degeneration in an anterior cruciate ligament transection model. *Osteoarthritis Cartilage* 23, 114-121 (2015).
50. X. Zhang, E. M. Schwarz, D. A. Young, J. E. Puzas, R. N. Rosier, R. J. O'Keefe, Cyclooxygenase-2 regulates mesenchymal cell differentiation into the osteoblast lineage and is critically involved in bone repair. *J Clin Invest* 109, 1405-1415 (2002).
51. P. Geusens, P. J. Emans, J. J. de Jong, J. van den Bergh, NSAIDs and fracture healing. *Curr Opin Rheumatol* 25, 524-531 (2013).
52. L. Claes, S. Recknagel, A. Ignatius, Fracture healing under healthy and inflammatory conditions. *Nat Rev Rheumatol* 8, 133-143 (2012).
53. M. M. Matzelle, M. A. Gallant, K. W. Condon, N. C. Walsh, C. A. Manning, G. S. Stein, J. B. Lian, D. B. Burr, E. M. Gravallese, Resolution of inflammation induces osteoblast function and regulates the Wnt signaling pathway. *Arthritis Rheum* 64, 1540-1550 (2012).
54. J. Chang, F. Liu, M. Lee, B. Wu, K. Ting, J. N. Zara, C. Soo, K. Al Hezaimi, W. Zou, X. Chen, D. J. Mooney, C. Y. Wang, NF-κB inhibits osteogenic differentiation of mesenchymal stem cells by promoting β-catenin degradation. *Proc Natl Acad Sci USA* 110, 9469-9474 (2013).
55. W. P. Arend, H. G. Welgus, R. C. Thompson, S. P. Eisenberg, Biological properties of recombinant human monocyte-derived interleukin 1 receptor antagonist. *J Clin Invest* 85, 1694-1697 (1990).
56. W. P. Arend, The balance between IL-1 and IL-1Ra in disease. *Cytokine Growth Factor Rev* 13, 323-340 (2002).
57. R. D. Howard, C. W. McIlwraith, G. W. Trotter, J. K. Nyborg, Cloning of equine interleukin 1 receptor antagonist and determination of its full-length cDNA sequence. *Am J Vet Res* 59, 712-716 (1998).
58. H. Kato, T. Ohashi, H. Matsushiro, T. Watari, R. Goitsuka, H. Tsujimoto, A. Hasegawa, Molecular cloning and functional expression of equine interleukin-1 receptor antagonist. *Vet Immunol Immunopathol* 56, 221-231 (1997).
59. M. K. Boyce, T. N. Trumble, C. S. Carlson, D. M. Groschen, K. A. Merritt, M. P. Brown, Non-terminal animal model of post-traumatic osteoarthritis induced by acute joint injury. *Osteoarthritis Cartilage* 21, 746-755 (2013).
60. C. E. Kawcak, D. D. Frisbie, N. M. Werpy, R. D. Park, C. W. McIlwraith, Effects of exercise vs experimental osteoarthritis on imaging outcomes. *Osteoarthritis Cartilage* 16, 1519-1525 (2008).
61. D. D. Frisbie, C. E. Kawcak, C. W. McIlwraith, N. M. Werpy, Evaluation of polysulfated glycosaminoglycan or sodium hyaluronan administered intra-articularly for treatment of horses with experimentally induced osteoarthritis. *Am J Vet Res* 70, 203-209 (2009).
62. D. C. Dymock, M. P. Brown, K. A. Merritt, T. N. Trumble, Concentrations of stromal cell-derived factor-1 in serum, plasma, and synovial fluid of horses with osteochondral injury. *Am J Vet Res* 75, 722-730 (2014).
63. C. W. McIlwraith, D. D. Frisbie, C. E. Kawcak, C. J. Fuller, M. Hurtig, A. Cruz, The OARSI histopathology initiative—recommendations for histological assessments of osteoarthritis in the horse. *Osteoarthritis Cartilage* 18 Suppl 3, S93-105 (2010).
64. C. Li, M. Hirsch, A. Asokan, B. Zeithaml, H. Ma, T. Kafri, R. J. Samulski, Adeno-associated virus type 2 (AAV2) capsid-specific cytotoxic T lymphocytes eliminate only vector-transduced cells coexpressing the AAV2 capsid in vivo. *J Virol* 81, 7540-7547 (2007).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

That which is claimed is:

1. A method of treating osteoarthritis in a subject, the method comprising:
   intra-articularly administering a pharmaceutical composition comprising:
   (a) a recombinant adeno-associated virus (rAAV) particle comprising a codon-modified gene encoding interleukin-1 receptor antagonist (IL-1Ra), and
   (b) a pharmaceutically acceptable carrier,
   wherein the codon-modified gene is selected from the group consisting of:
   (i) a codon-modified gene encoding human IL-1Ra and having a nucleotide sequence mismatch of 10-30% compared to the wild-type human IL-1Ra gene as set forth in SEQ ID NO: 9; and
   (ii) a codon-modified gene encoding equine IL-1Ra and having a nucleotide sequence mismatch of 10-30% compared to the wild-type equine IL-1Ra gene as set forth in SEQ ID NO: 1;
   wherein the codon-modified gene increases expression of IL-1Ra compared to a wild-type gene encoding IL-1Ra, and
   wherein the administering is to a joint of the subject to treat osteoarthritis.

2. The method of claim 1, wherein the subject is human.

3. The method of claim 1, wherein $1+10^{10}$ to $1 \times 10^{13}$ viral genomes (vgs) are administered to the joint.

4. The method of claim 3, wherein $1+10^{10}$ to $9\times10^{11}$ vgs are administered to the joint.

5. The method of claim 1, wherein the volume administered to the joint is 1-20 ml.

6. The method of claim 1, wherein the codon-modified gene encodes human IL-1Ra.

7. The method of claim 6, wherein the nucleotide sequence of the codon-modified gene is set forth in SEQ ID NO: 10.

8. The method of claim 1, wherein the codon-modified gene is preceded by a Kozak sequence, and wherein the Kozak sequence has a nucleotide sequence of GCCACC.

9. The method of claim 8, wherein the codon-modified gene increases expression of IL-1Ra protein levels 30-300 fold in a cell compared to a wild-type gene encoding IL-1Ra.

10. The method of claim 1, wherein the codon-modified gene encodes equine IL-1Ra.

11. The method of claim 10, wherein the nucleotide sequence of the codon-modified gene is set forth in SEQ ID NO: 2.

12. The method of claim 8, wherein the nucleotide sequence of the codon-modified gene is set forth in SEQ ID NO: 3.

13. The method of claim 8, wherein the nucleotide sequence of the codon-modified gene is set forth in SEQ ID NO: 11.

14. The method of claim 1, wherein the rAAV particle is of serotype 2 or 2.5.

15. The method of claim 1, wherein the rAAV particle is a self-complementary rAAV particle.

16. The method of claim 1, wherein the pharmaceutically acceptable carrier is a sterile liquid.

17. The method of claim 16, wherein the sterile liquid comprises water, an oil, or a saline solution.

18. The method of claim 1, wherein the pharmaceutical composition further comprises a liposome, a lipid, a lipid complex, a microsphere, a microparticle, a nanosphere, or a nanoparticle.

* * * * *

UNITED STATES PATENT AND TRADEMARK OFFICE
CERTIFICATE OF CORRECTION

PATENT NO. : 11,958,886 B2
APPLICATION NO. : 16/467141
DATED : April 16, 2024
INVENTOR(S) : Steven C. Ghivizzani It is certified that error appears in the above-identified patent and that said Letters Patent is hereby corrected as shown below:

In the Claims

At Column 48, Line 66, Claim 3:
"3. The method of claim 1, wherein $1+10^{10}$ to $1\times10^{13}$ viral"
Should read:
--3. The method of claim 1, wherein $1\times10^{10}$ to $1\times10^{13}$ viral--

At Column 49, Line 1, Claim 4:
"4. The method of claim 3, wherein $1+10^{10}$ to $9\times10^{11}$ vgs"
Should read:
--4. The method of claim 3, wherein $1\times10^{10}$ to $9\times10^{11}$ vgs--

Signed and Sealed this
Ninth Day of July, 2024

Katherine Kelly Vidal
*Director of the United States Patent and Trademark Office*